(12) United States Patent
Guirguis

(10) Patent No.: US 6,309,362 B1
(45) Date of Patent: *Oct. 30, 2001

(54) METHOD AND APPARATUS FOR AUTOMATICALLY SEPARATING PARTICULATE MATTER FROM A FLUID

(75) Inventor: Raouf A. Guirguis, Vienna, VA (US)

(73) Assignee: LaMina, Inc., Herndon, VA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/053,010

(22) Filed: Apr. 1, 1998

Related U.S. Application Data

(60) Continuation of application No. 08/474,894, filed on Jun. 7, 1995, now abandoned, which is a division of application No. 08/172,232, filed on Dec. 23, 1993, now Pat. No. 5,471,994, which is a division of application No. 07/920,662, filed on Jul. 28, 1992, now Pat. No. 5,301,685.
(60) Provisional application No. 60/058,008, filed on Aug. 5, 1997, and provisional application No. 60/056,445, filed on Aug. 25, 1997.

(51) Int. Cl.[7] ..................................................... A61B 5/00
(52) U.S. Cl. ........................ 600/573; 73/863.01; 422/63
(58) Field of Search ..................................... 600/573, 584; 604/317; 73/863.01, 863.23, 863.31; 422/58, 63–67, 68.1, 101, 102

(56) References Cited

U.S. PATENT DOCUMENTS

| | | | |
|---|---|---|---|
| 4,953,561 | 9/1990 | Guirguis | 128/771 |
| 5,016,644 | 5/1991 | Guirguis | 128/771 |
| 5,042,502 | 8/1991 | Guirguis | 128/771 |
| 5,137,031 | 8/1992 | Guirguis | 128/771 |
| 5,139,031 | 8/1992 | Guirguis | 128/771 |
| 5,143,627 | 9/1992 | Lapidus et al. | 210/767 |
| 5,224,489 | 7/1993 | Guirguis | 128/771 |
| 5,301,685 | 4/1994 | Guirguis | 128/760 |
| 5,441,071 | * 8/1995 | Doherty et al. | 137/15 |
| 5,441,699 | 8/1995 | So et al. | 422/63 |
| 5,471,994 | 12/1995 | Guirguis | 128/760 |

FOREIGN PATENT DOCUMENTS 0 740 142  10/1996 (EP) .
0 743 524  11/1996 (EP) .

* cited by examiner

*Primary Examiner*—Max Hindenburg
(74) *Attorney, Agent, or Firm*—Foley & Lardner

(57) ABSTRACT

An automated apparatus and method for batch processing a group of samples in respective containers. A monolayer of particulate matter is filtered from each sample and deposited on a corresponding slide for examination. A controller coordinates each mechanism and sub-assembly of the apparatus.

38 Claims, 17 Drawing Sheets

METHOD AND APPARATUS FOR AUTOMATICALLY SEPARATING PARTICULATE MATTER FROM A FLUID

CROSS-REFERENCES TO RELATED APPLICATIONS

The benefit of the earlier filing date for the present application under 35 U.S.C. § 120 is hereby claimed based on a continuation of U.S. application Ser. No. 08/474,894 filed Apr. 7, 1995 now abandoned; which is a divisional of U.S. application Ser. No. 08/172,232 filed Dec. 23, 1993 (now U.S. Pat. No. 5,471,994); which is a divisional of U.S. application Ser. No. 07/920,662 filed Jul. 28, 1992 (now U.S. Pat. No. 5,301,685). Moreover, the benefit of the earlier filing date for the present application under 35 U.S.C. § 119(e) is also claimed based on U.S. Provisional Application Ser. No. 60/058,008, filed Aug. 5, 1997, and titled "Method and Apparatus for Manually Separating Particulate Matter from a Fluid"; and on U.S. Provisional Application Ser. No. 60/056,445, filed Aug. 25, 1997, and titled "Method and Apparatus for Automatically Separating Particulate Matter from a Fluid".

BACKGROUND OF THE INVENTION

1. Field of the Invention

The present invention is directed to an improved apparatus and method for collecting a uniform monolayer of cells from body fluids suitable for use in improved automated cytological protocols.

2. Description of Related Art

In a wide variety of technologies, the ability and/or facility in separating matter, typically particulate matter, from a fluid is a critical component in the ability to test for the presence of substances in the fluid. Too often, interference associated with sample preparation obscures the target cells to such a degree that the process is not sufficiently reliable, or too costly.

A similar scenario applies to many other fields of examination which involve detection and/or diagnosis, including environmental testing, radiation research, cancer screening, cytological examination, microbiological testing, and hazardous waste contamination, to name just a few.

All that is required for a cytological examination of a sample is that a sample of cells be obtained from the patient, which can typically be done by scraping or swabbing an area, as in the case of cervical samples, or by collecting body fluids, such as those obtained from the chest cavity, bladder, or spinal canal, or by fine needle aspiration. In a conventional manual cytological examination, the cells in the fluid are then transferred onto a glass slide for viewing. In a conventional automated cytological examination, a filter assembly is placed in the liquid suspension and the filter assembly both disperses the cells and captures the cells on the filter, and the filter is removed and placed in contact with a microscope slide.

In all of these endeavors, a limiting factor in the sample preparation protocol is adequately separating solid matter from its fluid carrier (e.g., a variety of fluids, such as physiological, biological and environmental), and in easily and efficiently collecting and concentrating the solid matter in a form readily accessible to microscopic examination.

Prompt processing of urine to obtain fresh cells traditionally has been recommended to ensure the accuracy of quantitative culture results, urinalysis and microscopy. Fresh cells tend to stick to a glass slide much better than cells from preserved urine, allowing for smoother cell spread onto the glass body. Delays in processing, negligent care in either inpatient or outpatient settings and lack of refrigeration may lead to non-optimal slide preparation. One known solution to the delay problem is the use of chemical preservatives with the urine. The presence of liquid preservatives, however, in the urine specimen raises the specific gravity of the specimen to unmeasurable levels and may limit the potential usefulness of the urine for various types of traditional quantitative analysis, such as slide microscopy.

A number of urine or other biological fluid specimen containers have been developed to allow liquid biological specimens to be tested without removing the lid of the urine or biological fluid container. None of the prior art solves the problems of transferring cells in a monolayer to a slide for examination without submerging portions of the device in the sample (and increasing the risk of contamination), consistently and repeatedly forming a high quality monolayer on the microscope slide, and processing the sample so that the fluid from which the cells were taken is preserved.

Currently, body fluid samples are collected for cytological examinations using special containers. These containers usually contain a preservative solution for preserving the cytology specimen during shipment from the collection site to the cytology laboratory. Furthermore, cytology specimens collected from the body cavities using a swab, smear, flush or brush are also preserved in special containers with fixatives (e.g., alcohol or acetone fixatives) prior to transferring cells onto the slide or membrane for staining or examination.

Diagnostic microbiology and/or cytology, particularly in the area of clinical pathology, bases diagnoses on a microscopic examination of cells and other microscopic analyses. The accuracy of the diagnosis and the preparation of optimally interpretable specimens typically depends upon adequate sample preparation. New methodologies such as immunocytochemistry and image analysis require preparations that are reproducible, fast, biohazard-free and inexpensive. Different cell preparation techniques of the present invention address the issues of non-uniform cell densities, uneven cell distribution and air drying artifacts. These preparations have resulted in an even distribution of cells that have superior morphology, which has improved light microscopic visualization and has allowed for the use of image cytometry instruments.

In contrast to the conventional techniques, the solid matter preparation techniques of the present invention address the issues of non-uniform matter densities, uneven matter distribution, and sample loss due to the number of steps involved in the sample preparation. Thus, preparations according to the present invention result in an even distribution of solids that have superior morphology, improved visualization, and are readily positioned and available for light absorbance analysis without the need to further manipulate or prepare the sample.

SUMMARY OF THE INVENTION

The present invention relates to an apparatus and method for collecting matter for detection, analysis, quantification, and/or visualization. The automated devices and methods of the present invention are particularly suitable for separating matter from biological, physiological, and environmental fluids and presenting the particulate matter in an improved manner for cytological examination.

The present invention relates to an automated apparatus and method for collecting a uniform layer of cells from urine or other fluid specimen in a cytology collection apparatus or assay module, which can be removably detached from a collection container for application to a slide. An instrument according to the invention resolves problems associated with known equipment for collecting cells and other particles for cytology by providing a mechanism of relatively simple structure and operation that separates particles from a liquid solution, collects an approximately known quantity of the cells in a monolayer, and transfers the collected cells to a microscope slide. In some embodiments of the invention, no element of the apparatus is placed in the liquid sample, thus preventing unnecessary contamination of the sample. In all embodiments of the invention, a monolayer of the particulate matter, e.g., cells, in the sample is collected on a filter by passing two branches of a fluid flow through and around the filter.

According to one embodiment of the present invention, the collection of a monolayer of cells for cytological examination allows a uniform cell slide to be obtained without contamination of the cells by preservatives, workers or outside materials. The transfer of cells from a sample container to the cytology collection apparatus may be carried out without pouring or pipetting the collected specimen.

The present invention is directed to a cell collection and distribution apparatus which can be easily disassembled to allow face-to-face transfer of cells from the device to a slide for microscope examination. The present invention provides an improved apparatus and method for collecting a monolayer of cells which can be transferred to a microscope slide.

The devices of the present invention obviate the need for a trained technician to properly prepare a sample substrate. Thus, time, expense and expertise are eliminated or reduced as critical factors in sample preparation protocols.

The devices and methods of the present invention also provide advantages in sample preparation because they are suitable for use with fresh, untreated cells, unmodified cells, and are particularly designed to provide a thin, uniform layer of solid matter (up to approximately 40 microns or more). This invention is particularly useful for collecting cells for a pap smear.

According to another aspect of the present invention, the matter collection apparatus may also include additional modules, removable or integrated, for treating the fluid. For example, the fluid may be treated with a matter collection module, in combination with a debris removal module, a chromatography module, an assay module, or combinations of these and other devices. These and other modules or treatment protocols provide features which may be desirable to incorporate into a sample preparation apparatus according to the invention.

For example, the devices and methods of the present invention have many advantages for conventional microbiology and hematology. The collected cells are in a predetermined area easily accessible to a radiant light source and to a wavelength absorbance meter. Because cells are concentrated in a single layer, they are almost always in one focal plane, thus eliminating or reducing interference by other particles and virtually eliminating technician time and expertise in establishing a proper reading. The minimal matter overlap achieved ensures that all matter can be easily examined with little chance for critical solids to be obscured by clumps of overlapping solids or debris. Certain embodiments of the apparatus of the present invention even permit the use of automated devices to detect and analyze any solid matter in a given population. They also permit a detailed analysis of the chemical composition of the matter.

The effectiveness of transferring the monolayer cells from the filter to a microscope slide has proven to be very high without differential cell loss. Microscopic examination shows that the cell distribution is substantially the same on the slide as on the filter.

The apparatus includes at least one sample container mounted on a transport. In one embodiment of the invention, the cap of the sample container may include a hollow tube with or without a rotatable dispersing element. Movement of the transport may rotate the dispersing element. A preferred transport provides both lateral movement, for carrying the sample container and a cell transfer mechanism from one location to another, and vertical movement, as for removing the filter assembly and positioning the filter assembly in contact with a microscope slide assembly. In a preferred embodiment of the invention, the automated apparatus includes a platform having a plurality of filter assemblies, a platform for positioning a plurality of specimen containers, a platform for positioning a plurality of microscope slides and/or filters, a filter loader adjacent to the filter assembly platform, a microscope slide loader adjacent to the microscope slide platform, a microscope slide unloader adjacent to the microscope slide platform, and a control system for operating, monitoring, and sequencing the various assemblies.

The control system monitors the particulate matter collecting operation by monitoring parameters of the liquid flow to determine when a pre-determined quantity of particulate is collected on the filter. An upper assembly of the instrument positions the filter device, with the collected cells on the filter surface, for abutment against a microscope slide.

It is important to the method and apparatus of the invention that the cells maintain the monolayer distribution with which they were collected on the filter as the cells are transferred from the filter device to the microscope slide. The invention thus provides cell collection and transfer means that produce a monolayer of cells on the microscope slide.

An instrument according to the present invention preferably employs a fresh sample vial, an unused filter assembly, and an unused microscope slide for each individual cell specimen. Moreover, the relatively simple operation, and the multiple functions which the instrument performs, minimize the requirements for operator attendance and time, as well as minimizing maintenance and preparation.

An embodiment of the invention includes a movable sample container platform, a sample container having a cap adapted to matingly engage a filter assembly, a movable filter assembly platform, one or more microscope slide loader/unloader assemblies adapted to engage the filter, and a microscope slide positioned on the microscope slide loader/unloader assembly. A preferred embodiment of the invention includes multiple iterations of each of the subassemblies described above, so that a preferred automated apparatus according to the invention can process at least two, typically five or more, specimens at the same time or sequentially.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

FIG. 9b is a side view of the assembly illustrated in FIG. 9a.

DETAILED DESCRIPTION

Figure 1:
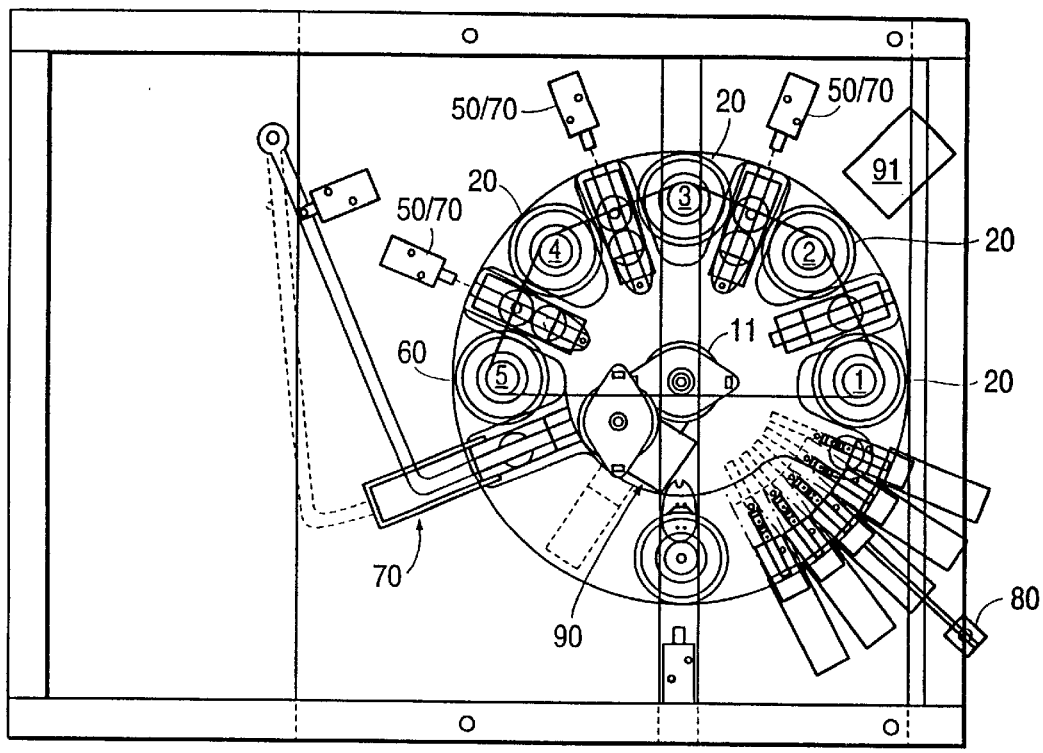
FIG. 1 is a top view of an exemplary embodiment of the invention.

An apparatus according to the present invention is an automated collection of assemblies or mechanisms for batch processing samples. The apparatus according to the present invention is particularly useful for removing particulate matter from a liquid and transferring the particulate matter to a microscope slide or other cytological examination element. During operation of the automated apparatus, processing of the liquid, particulate matter, or the sample container containing the sample may include or involve one or more of the following stages or steps: opening the container used to ship or transport the sample to the site of the automated apparatus; attaching a sample container cover that extends into the sample; positioning a filter assembly with respect to the cover for fluid communication with the sample; withdrawing at least a portion of the sample from the container through the filter assembly whereby a portion of the particulate matter contained in the sample is adhered to a membrane in the filter assembly; providing a microscope slide movable to a position adjacent to, aligned with, and/or resting against a portion of the filter assembly. Additionally, mechanisms and/or sub-assemblies may further include: one or more sub-assemblies for replacing a used microscope slide with an unused microscope slide; a movement transmission for stirring the sample; one or more filter assembly loaders; one or more filter assembly unloaders; one or more microscope slide loaders; one or more microscope slide unloaders; one or more bar code readers; one or more bar code printers; one or more transport mechanisms for moving and/or positioning one of the structures noted above; one or more supports for retaining, positioning, or moving one or more of the structures noted above; one or more motors for moving or positioning one or more of the structures noted above; and one or more control systems for operating, preferably selectively and/or sequentially, one or more of the various structures noted above.

The present invention also involves a method for processing a liquid containing particulate matter, e.g., cells, using an automated apparatus configured according to the invention. The present invention also involves removing particulate matter from a liquid and collecting the particulate matter on a medium suitable for cytological examination of the particulate matter.

The present invention also includes automated devices and methods for collecting fluids, such as biological, physiological, or environmental fluids, removing particulate matter from the fluid, without centrifugation, and diagnosing and testing the matter.

As used herein, "sample" refers to any fluid in combination with solid matter, such as particulate matter, and from which it may be desirable to collect the particulate component from the sample for the purpose of establishing its identity or presence in the sample. Typically, the fluid component of the sample will be a liquid. However, the fluid may also be air or gas. As an example, it may be desirable to determine the presence of cancer cells or certain proteins in the biological fluid, such as urine. In another example, it may be desirable to evaluate the nature of contaminants, such as molecular contaminants, in ultra-pure water used in the electronics industry. Other exemplary fluids include but are not limited to body fluids, such as blood, spinal fluid, or amniotic fluid; bronchial lavage; sputum; fine needle aspirates; ground water; industrial processing fluids; and electronic or medical dialysis fluids, to identify just a few. It is intended that the invention should not be limited by the type of fluid being processed.

As used herein, "particulate matter" refers to any substance in a fluid which is capable of collection and evaluation, preferably by cytological examination. Exemplary matter includes, but is not limited to cells or cell fragments, proteins, molecules, polymers, rubbers, stabilizers, antioxidants, accelerators, silicones, alkyds, thiokols, paraffins, thermoplastics, bacteria, pesticides, and herbicides. Specific exemplary polymeric matter includes, but is not limited to polyethylene, polypropylene, polyisobutylene, polyacrylonitrile, polyethylene glycol, polyvinylchloride, polystyrene, polysulfide, polymethylmethacrylates, polyethyleneterephthalates, bisphenol A (a common environmental contaminant), ethyl cellulose, nitrocellulose, polyurethane, and nylon. Specific exemplary biological matter includes cancer cells, including distinguishing between metastatic and normal cancer cells; proteins, nucleic acids, antibodies, or the like. It is intended that the invention should not be limited by the type of matter being processed.

As used herein, "adapted for communication", "communicating", or similar terms refer to any means, structures, or methods for establishing fluid flow through the system, as are well known by practitioners in the art. Exemplary structures are shown in the Figures. For example, a conduit may have a connector adapted to receive or connect to a mated connector on another conduit. As used herein, connector refers to any structure used to form a joint or to join itself to another piece. These connectors or connections establish a fluid flow path through various elements of the apparatus, assembly, or system. Typical connections include but are not limited to mating connections, such as Luer-type, screw-type, friction-type, or connectors that are bonded together.

As used herein, "adapted for engaging", "engagement", "engaging", or similar terms refers to complementary structures that may align, mesh, mate, or rest near, against, or within each other. Exemplary structures include the connectors described above.

As used herein, "batch processing" refers to an operation or operations that are capable of being performed independently and simultaneously on more than one sample without cross-contamination between the samples.

As used herein, "group" refers to a quantity of examples of a feature that are identically and concurrently acted upon or utilized in the course of batch processing. A partial group refers to at least one, but less than a maximum finite number of example of the feature, and a full group refers to the maximum finite number of examples of the feature.

Sample Container, Cover, and Support

In accordance with the invention, a sample is collected using conventional techniques, e.g., by collecting urine or other biological fluid in a specimen container, or by placing a swab or brush in a suitable fluid in the specimen container (as is typical for a PAP smear). In a most preferred embodiment of the invention, the specimen or sample is collected in a sample container having the design and function as described below. The sample container is typically covered, and has a portion which may be suitable for engaging a filter assembly. In preferred embodiments of the invention, the container includes a central recessed portion adapted to receive the filter assembly. In some embodiments of the invention, the central recessed portion also communicates with or engages a hollow tube that extends into the specimen container. Optionally, a portion of the tube may include a stirring or dispersing element.

A group of the specimen containers is then positioned by hand or mechanically on a container support for further processing in an automated apparatus according to the invention. The container support is preferably a substantially planar platform, disc, sheet, shelf, tray, or the like. In preferred embodiments of the invention, a sample container includes guides suitable for positioning and/or retaining one or more specimen containers. In more preferred embodiments of the invention, the container support includes one or more recesses or cavities adapted to accommodate at least one size of sample container. In a most preferred embodiment of the invention, the container support includes at least two recesses for accommodating a least two different size sample containers. The container support is preferably movable, i.e., adapted to rotate around an axis of be translated along a path. In accordance with the invention, the container support is movable to determined positions or stages, including one or more stages that align a portion or portions of the support adjacent to or in proximity to another element of the automated apparatus, e.g., a loader or unloader.

In preferred embodiments of the invention, a specimen cup includes a chamber for collecting a liquid specimen and a cover that establishes fluid communication between the chamber and a filter assembly for separating particulate matter from the fluid and collecting the particulate matter at a collection site. In most preferred embodiments of the invention, the separated particulate matter is collected in a monolayer on a membrane according to the invention. Preferred embodiments of the invention also include a cover having a hollow tube establishing fluid communication between the sample and the filter assembly. More preferably, the hollow tube includes means for mixing the specimen and/or dispersing the particulate matter in the specimen.

In accordance with preferred embodiments of the invention, a specimen container 20 includes any container suitable for holding a fluid, preferably a biological fluid. The container 20 includes side walls 21 and bottom wall 22 that, in combination, provide a chamber 23 having an open end 24, for collecting, holding, or storing a fluid. Typical fluids include, but are not limited to biological fluids, such as body fluids, waste water fluids, or the like. Typical body fluids include urine or other biological fluids, such as blood, cerebrospinal fluid (CSF), bronchial lavage, sputum or fine needle aspirates.

The configuration and materials used to make the cup can be any of a variety of materials, shapes, and sizes. For example, the cup can be constructed of any material compatible with the fluid to be processed. It will be appreciated that the container and the assembly of the side walls to the bottom wall can be any conventional assembly. In more preferred embodiments of the invention, bottom wall 22 is a conical member, as shown in FIG. 20.

In accordance with a preferred embodiment of the present invention, specimen container 20 includes a tube 25 or the like for drawing the sample from within the container 20. Preferably, tube 25 will be hollow and open or openable at both ends. Tube 25 as illustrated includes open end 26 near the bottom of the container 20, and may include one or more apertures 27 into tube 25 . Open end 26 and/or apertures 27 permit different fluid layers as well as particulate matter and sediments to be simultaneously tested when the sample is withdrawn from the collection chamber 23.

Figure 20:
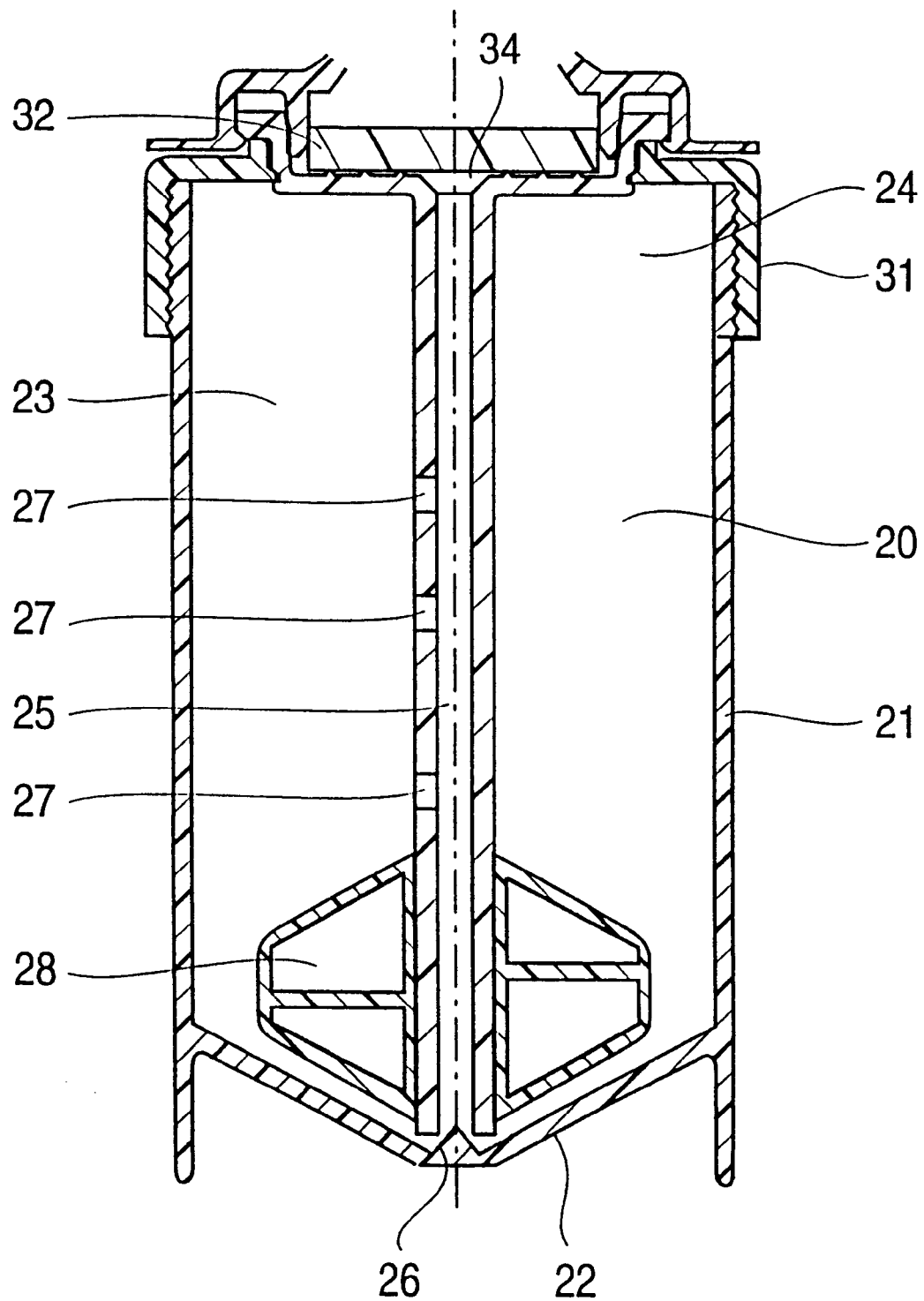
FIG. 20 is a side view of an exemplary specimen container, including a stirring mechanism, according to an embodiment of the invention.
Figure 21:
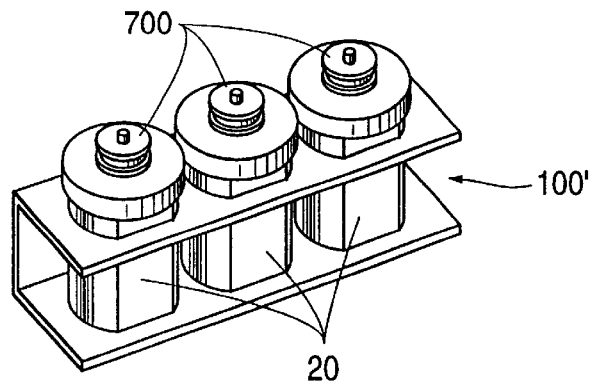
FIG. 21 is a perspective view of an exemplary container support according to an embodiment of the invention.

In accordance with another embodiment of the improved invention, hollow tube 25 includes at least one agitator projection or fin 28 or the like, as shown in FIG. 20. In a preferred embodiment of the invention, hollow tube 25 is rotatable and agitator 28 stirs the liquid specimen, and in a most preferred embodiment, disperses cells and/or particulate matter, and/or disrupts any large particulate matter such as mucoid bodies. Agitator 28 may also include a body that is independent of the tube 25, and that is induced by a magnetic or electric field to stir the sample.

Filter Assembly and Head

An apparatus according to the invention also includes a group of head assemblies adapted to engage a portion of corresponding specimen containers. According to preferred embodiments of the invention, the number and arrangement or pattern of the groups of heads and specimen containers correspond with one another. In preferred embodiments of the invention, each head assembly includes a portion having a cavity receiving or engaging a filter as described below. In most preferred embodiments, a portion of the filter head assembly matingly and removably engages a portion of the cover, and in mating engagement, forms a chamber adapted to position and accommodate a filter assembly. In accordance with the invention, the filter assembly and chamber provide at least two fluid flow branches through the chamber. A portion of the filter head assembly is preferably movable in a direction to engage the specimen containers on the container support. In accordance with preferred embodiments of the invention, container supports are sequentially moved with respect to a stationary reference frame into a position to be engaged by the filter head, and the filter head assembly is not displaced with respect to the stationary reference frame.

In other preferred embodiments of the invention, an adapter fitting is interposed between the container and the respective head and forms at least a portion of the filter chamber. The adapter fitting may be included with each container, or a group of adapters may be respectively associated with the corresponding group of heads.

Each head assembly is connected to a pump or the like. In this embodiment of the invention, the various structures provide a fluid flow path from the specimen container, through the filter in the filter chamber, and away from the specimen container toward the pump.

Figure 2:
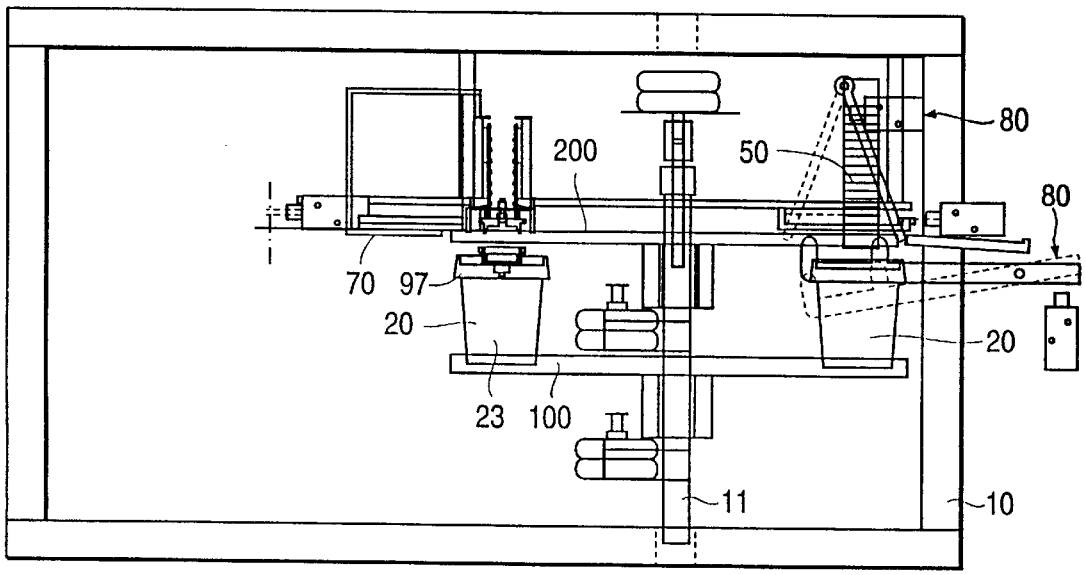
FIG. 2 is a side view of the exemplary embodiment illustrated in FIG. 1.
Figure 10:
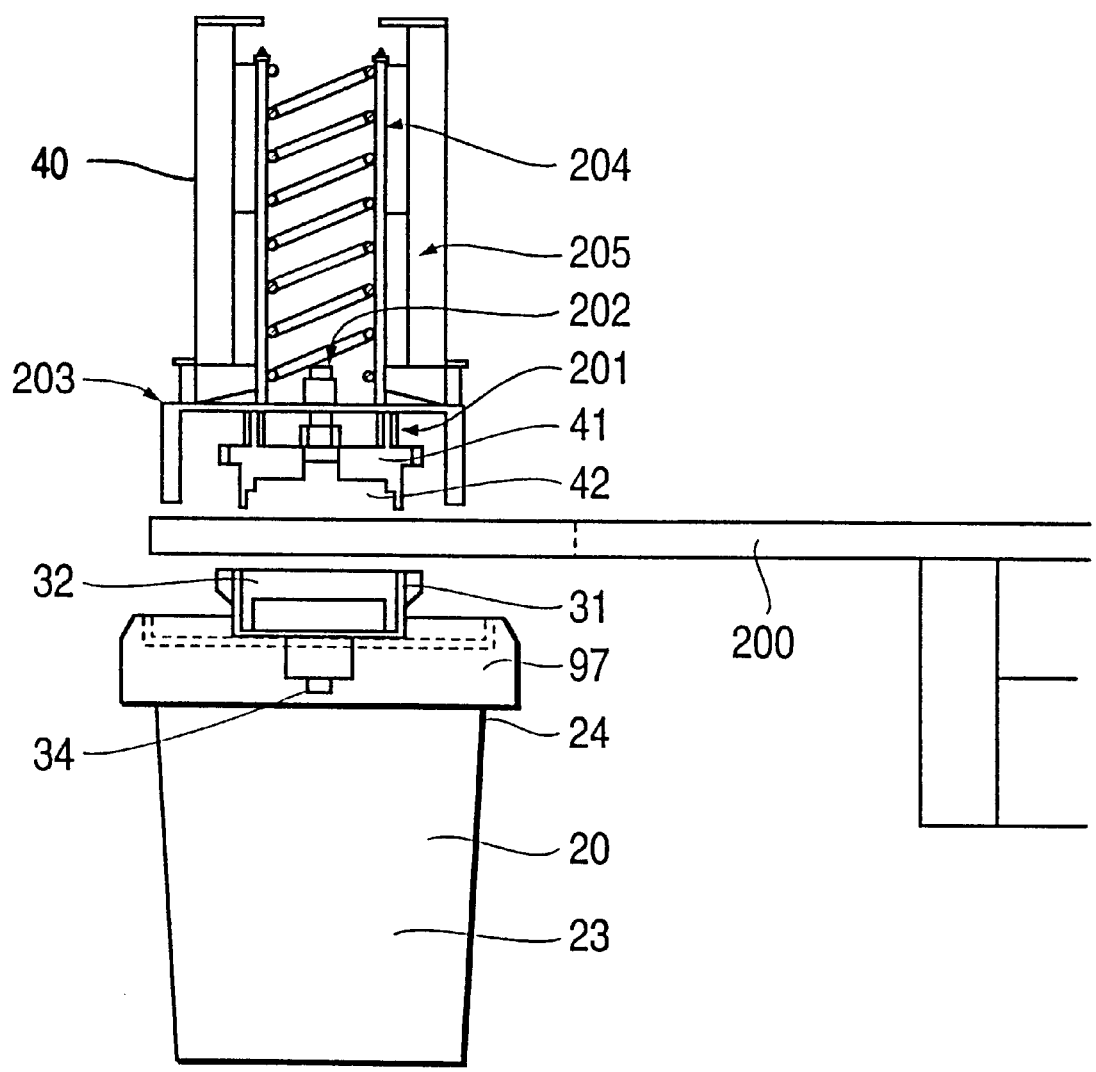
FIG. 10 is an exploded side view of a detail of the filter assembly and a specimen container according to an embodiment of the invention.
Figure 14:
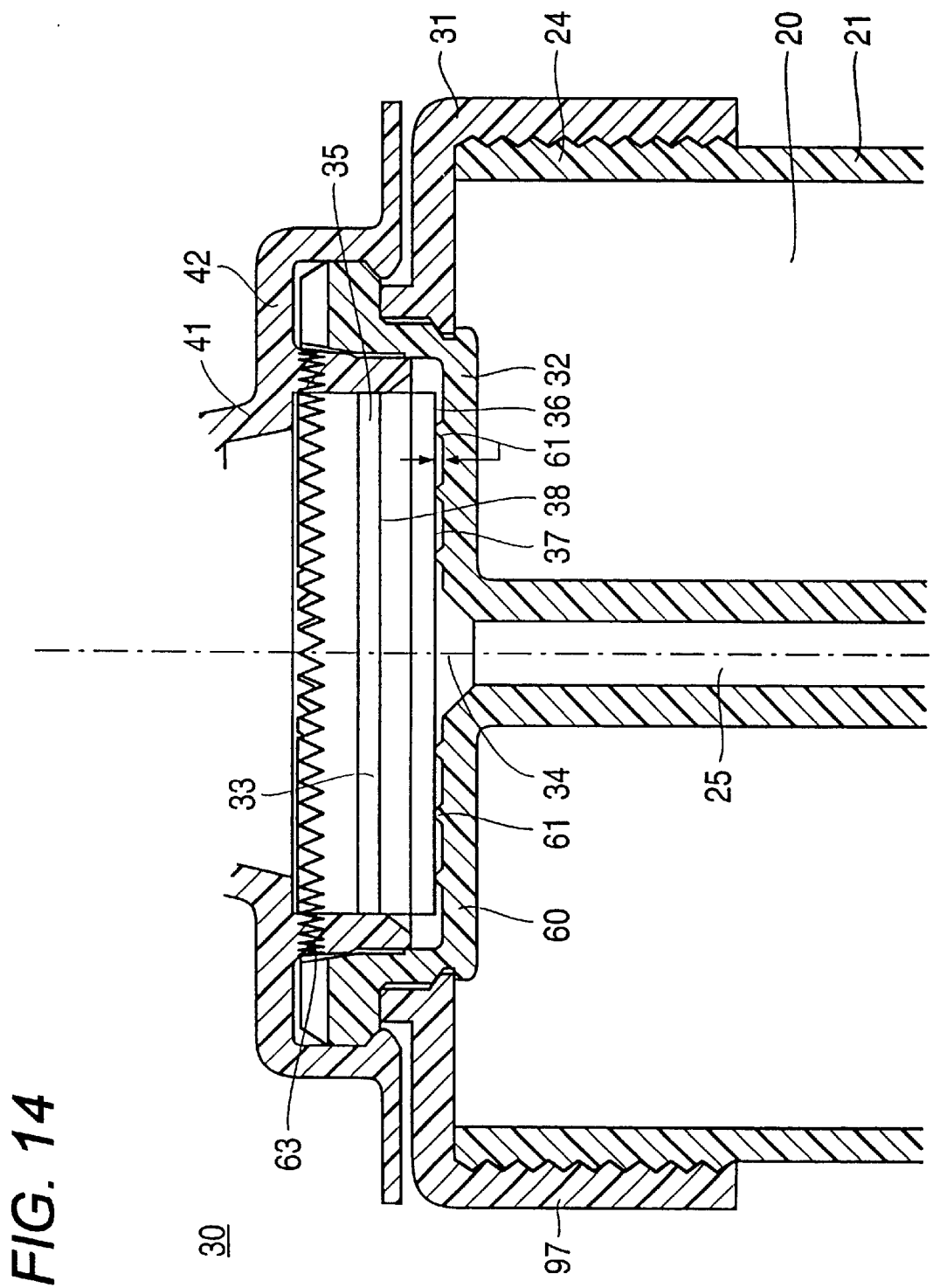
FIG. 14 is a side view of the filter assembly in its closed position according to an embodiment of the invention.
Figure 15:
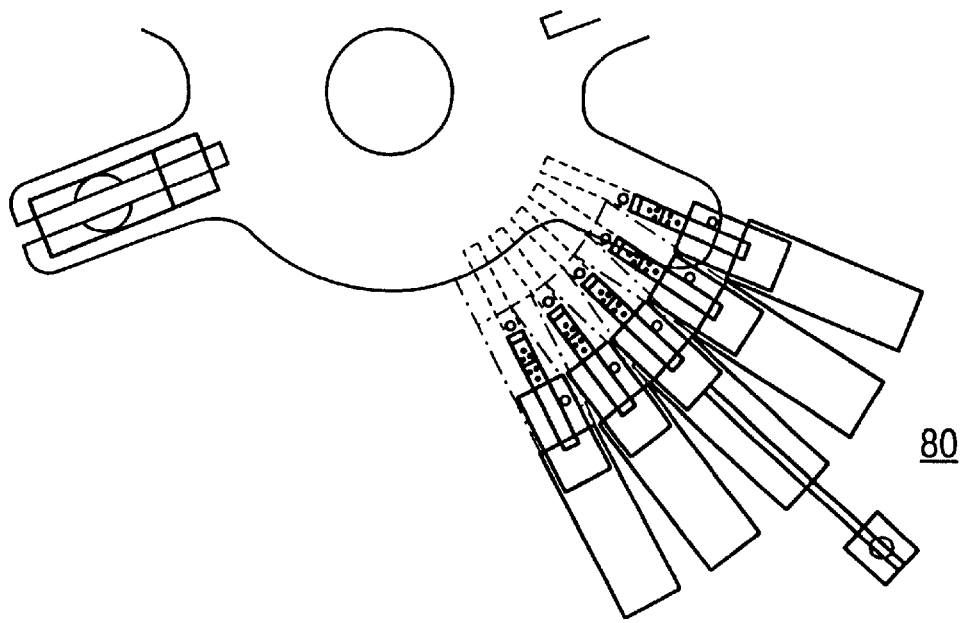
FIG. 15 is a top view of a microscope slide unloader assembly according to an embodiment of the invention.
Figure 16:
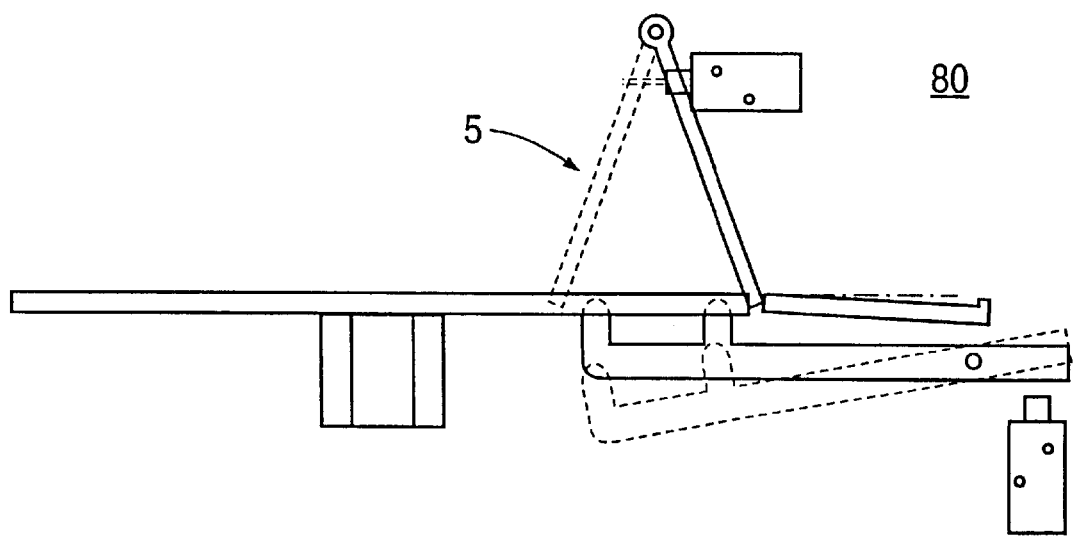
FIG. 16 is a side view of the assembly illustrated in FIG. 15.
Figure 17:
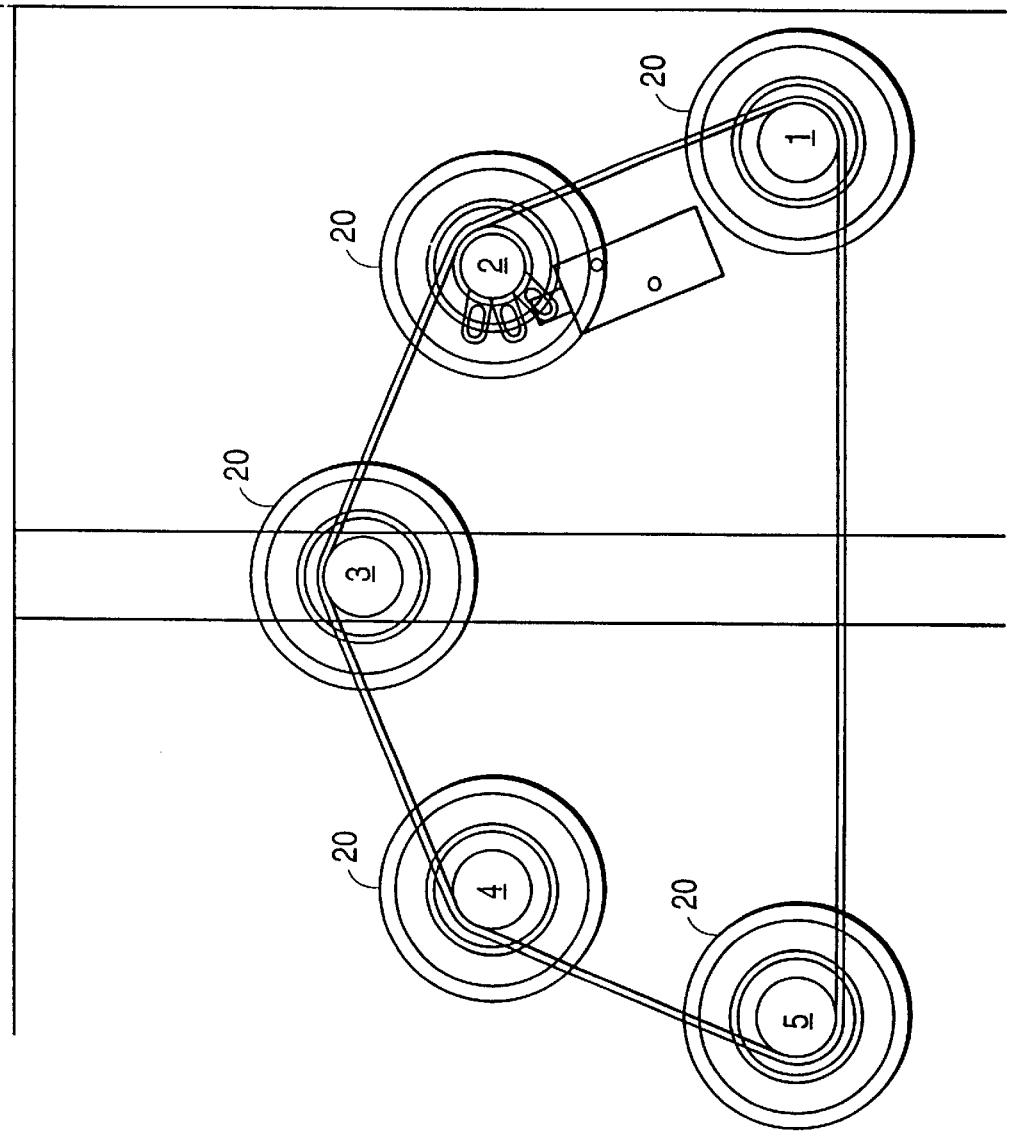
FIG. 17 is a top view of a stirring assembly according to an embodiment of the invention.
Figure 18:
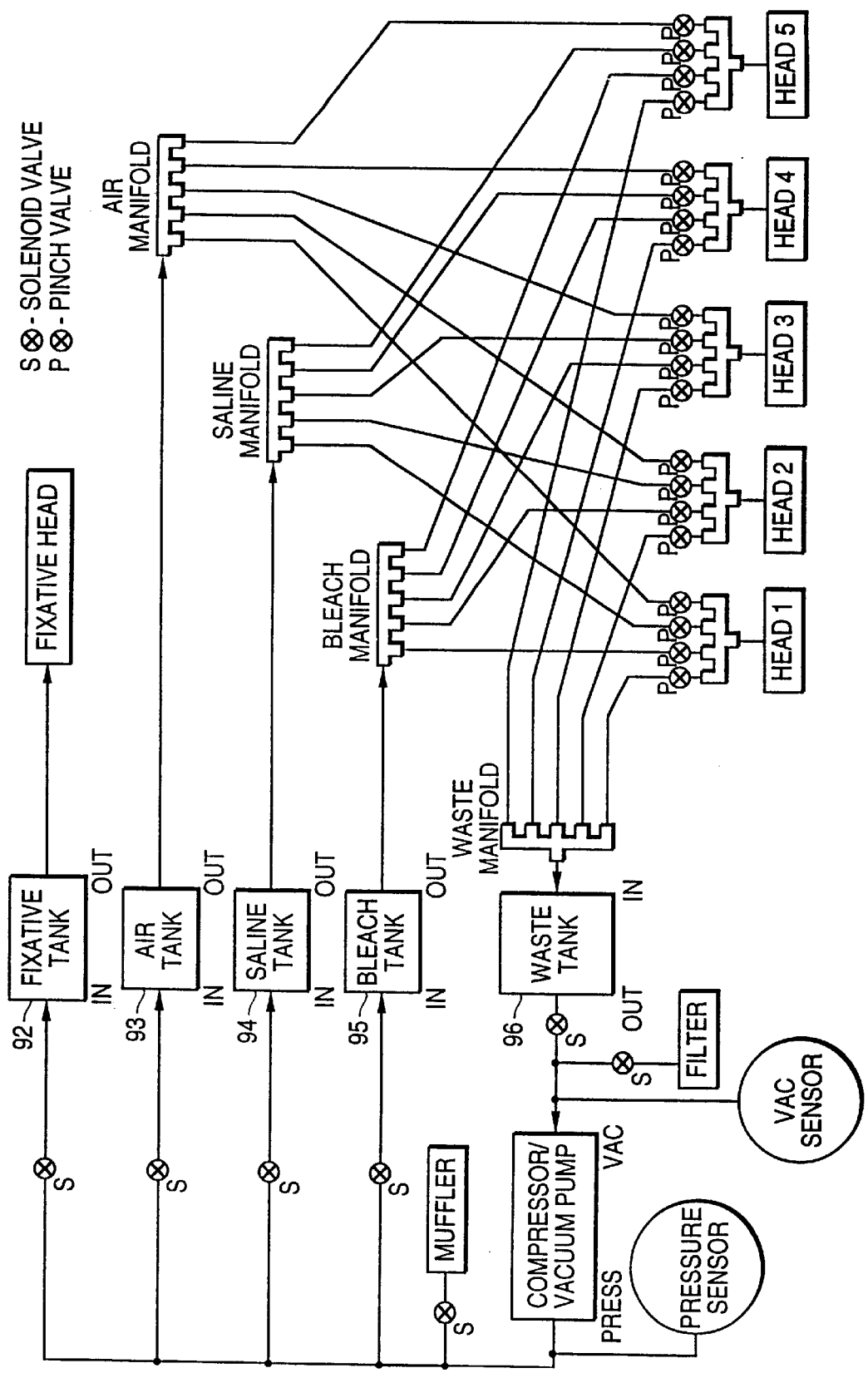
FIG. 18 is a schematic illustration of an exemplary fluid management system according to an embodiment of the invention.
Figure 19:
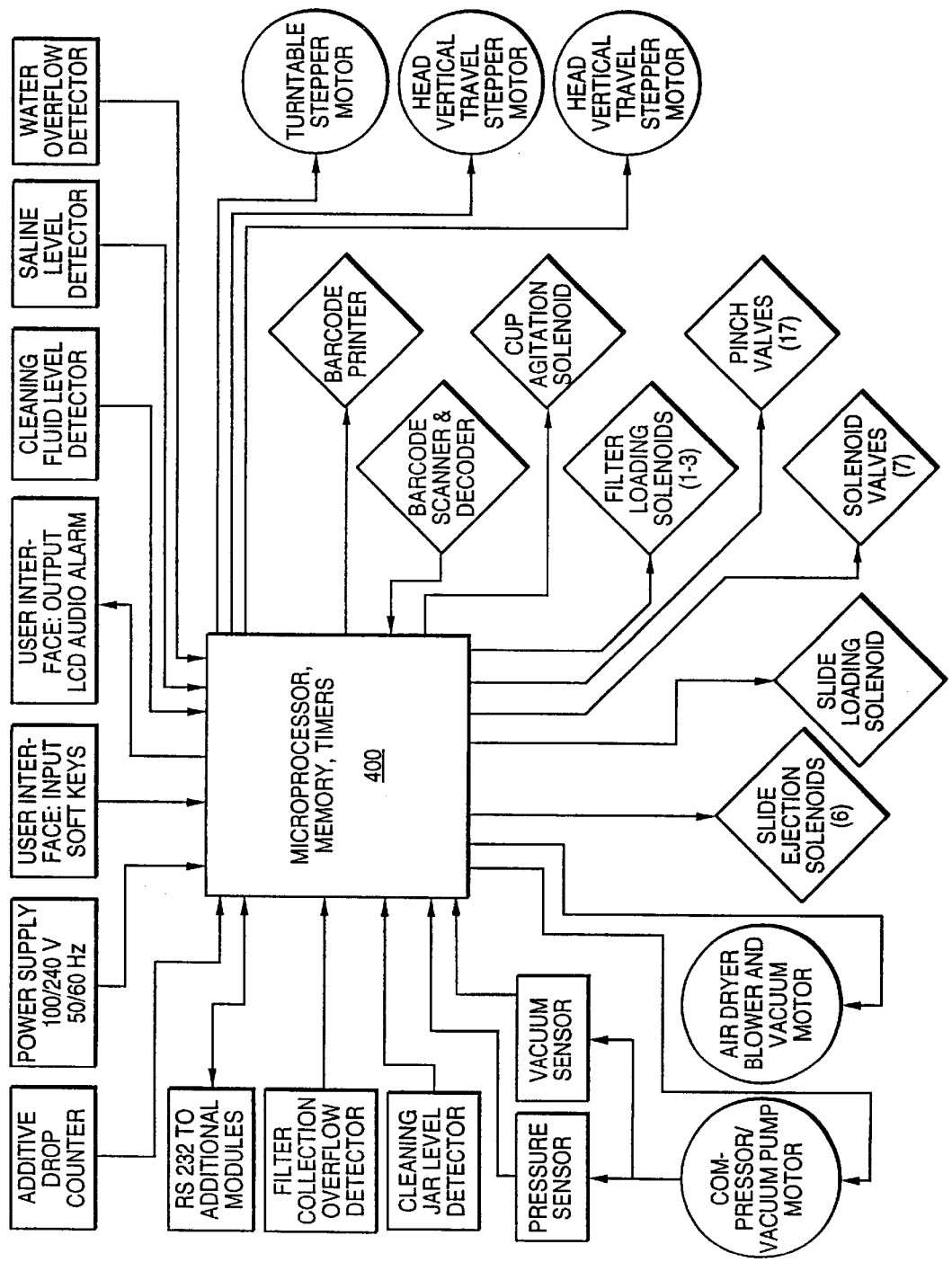
FIG. 19 is a schematic illustration of an exemplary control system according to an embodiment of the invention.

As noted above, an upper portion of the container and a lower portion of each head assembly matingly form a filter chamber. The containers and heads may be variously configured. Exemplary configurations are shown in FIG. 2, 10, and 14. In preferred embodiments of the invention, the chamber 30 includes a base portion 31 formed in part from or engaged with the cover of the specimen container 20.

Base portion 31 also defines a well 32 suitable for seating a filter assembly 33. Well 32 is provided with a channel 34 or the like communicating with hollow tube 25. Well 32 may be an integral structure of base 31, or may be a separate structure. In preferred embodiments of the invention, well 32 is a separate structure that is capable of rotating in the base 31. In order to achieve ease of relative rotation while maintaining a fluid-tight assembly, well 32 may matingly engage base 31 through a tongue and groove arrangement (see FIG. 14).

In accordance with the invention, the filter assembly chamber 30 is configured to receive a porous arrangement 35 having a particulate matter collection site 36 adapted to collect particulate matter as the sample containing the particulate matter passes through the chamber 30.

Porous arrangement 35 having a collection site 36 adapted to collect matter may be positioned in the fluid flow path such that the collection site 36 communicates with hollow tube 25. The porous arrangement 35 within the filter chamber is preferably adapted to define first and second branches of the fluid flow path. The first branch 39a extends through the collection site 36 and the second branch 39b bypasses the collection site 36 (see FIG. 13).

In preferred embodiments of the invention, the porous arrangement 35 includes a first porous medium 37, suitable for preventing the passage of matter therethrough, and a second porous medium 38, suitable for allowing the sample to pass therethrough. The second porous medium may or may not be capable of removing particulate matter from the sample, according to the needs of a particular device. In more preferred embodiments of the invention, the first porous medium is suitable for capturing or collecting particulate matter, and even more preferably, capturing or collecting solid matter in a uniform, single layer, i.e. a monolayer. Preferred embodiments also include a second porous medium which is suitable as a support for the first porous medium.

Preferred porous media are disclosed in U.S. Pat. No. 5,301,685, U.S. Pat. No. 5,471,994, incorporated herein by reference, and in Provisional application Ser. No. 60/058, 008 (filed Aug. 5, 1997, and titled "A Method and Apparatus for Manually Separating Particulate Matter from a Fluid"), also incorporated herein by reference.

The nature of the material used to make the porous media, the compatibility of the materials chosen for the porous media with one another and with the liquid to be processed are all factors to be considered in selecting a particular material for a porous medium for a given application.

The first porous medium and the second porous medium may be positioned in any fashion that functions as described herein. As one skilled in the art will recognize, the porous arrangement may be variously configured and positioned as needed to achieve a particular result. For example, the first and second porous media may be separate, spaced apart media; the two media can be laminated together; the first medium can be integral with or removably engaged with the second porous medium; or the collection element may comprise a zone of higher density which mimics the function of the first porous medium as described above, and a zone of lower density which mimics the function of the second porous medium as described above. Choice of these various configurations is well within the skill of practitioners in the art. Variations on the structure and composition of the porous arrangement will be described in more detail below.

As shown in FIGS. 10 and 14, the filter chamber 30 is preferably a two-piece housing formed by a top portion 41 at a lower end of a head, and a base portion 31 at a portion of the specimen container. In preferred embodiments of the invention, top portion 41 releasably engages base portion 31; any housing configuration or assembly providing access to the porous arrangement 35 is suitable. Top portion 41 and base portion 31 may be connected or fastened to each other by any mating connection or means that provides a fluid-tight fit, e.g., Luer-type (threaded or not threaded), screw thread-type, friction-type, a tapered mating connection, or snap fit (as illustrated).

Figure 11:
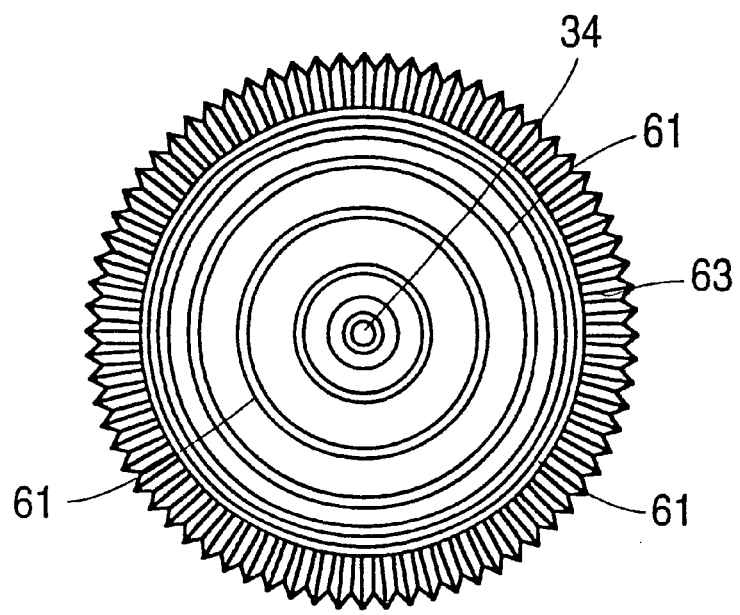
FIG. 11 is a top view of a detail of the filter assembly according to an embodiment of the invention.
Figure 12:
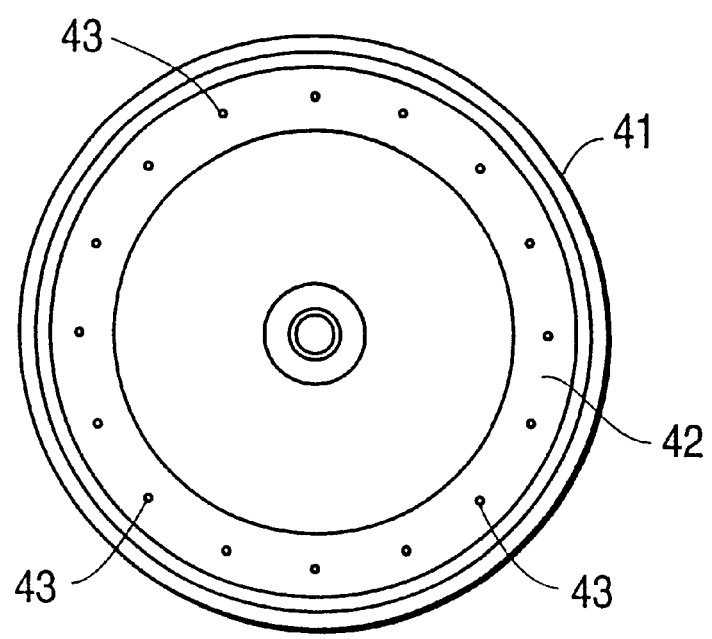
FIG. 12 is a bottom view of a detail of the filter assembly according to an embodiment of the invention.

In accordance with preferred embodiments of the invention, the well 32 of base 31 includes a seat 60 with one more spaced apart projections 61 or the like. Projections 61 are preferably of a size and shape sufficient to prevent porous arrangement 35 from flushly contacting seat 47. In the illustrated embodiment, projections 61 are concentric rings (see FIG. 11). As will be described in more detail below, projections 61 break the surface tension between porous arrangement 35 and seat 60 so that, during use, when porous arrangement 35 is pulled away from seat 60, first porous medium 36 does not remain in contact with seat 60.

Figure 4:
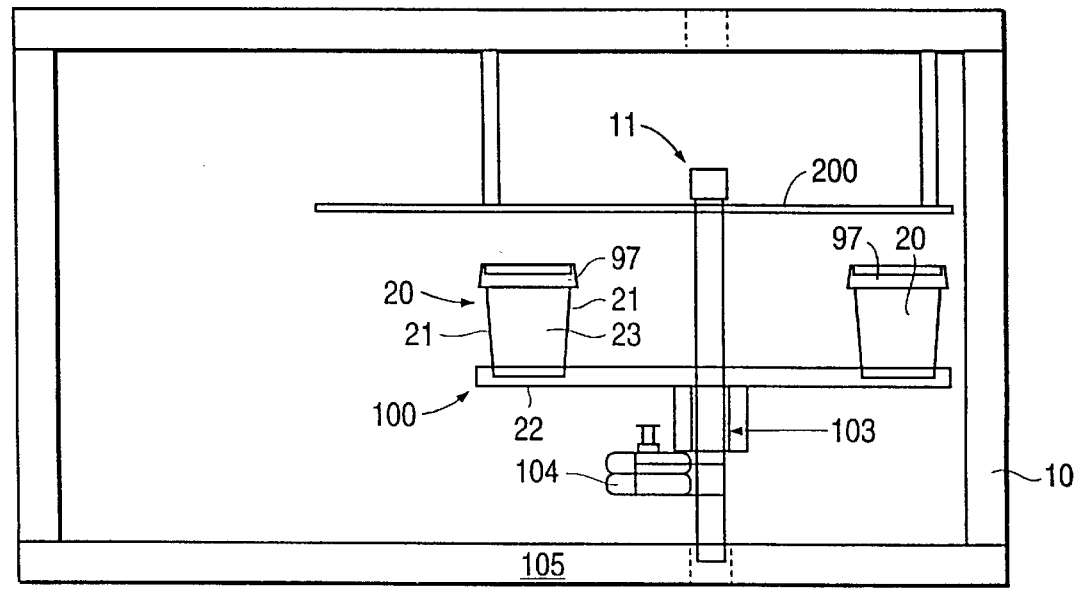
FIG. 4 is a side view of the assembly illustrated in FIG. 3.

In preferred embodiments of the invention, the filter head assembly includes a top portion 41 that engages base 31, and in combination, forms filter chamber 30. Portion 41 includes a seat 42 or the like configured to engage porous arrangement 35. In preferred embodiments of the invention, seat 42 positions porous arrangement 35 in well 32 so that porous arrangement 35 does not move while the sample is being drawn from its respective container. In most preferred embodiments of the invention, seat 42 includes a plurality of projections or posts 43 of a size, shape, and number so as to position the filter assembly in the filter chamber 30, to promote substantially even distribution of pressure against the porous arrangement, and to reduce or prevent compression of the porous arrangement that would interfere with fluid flow through the porous arrangement. Alternatively or additionally, porous arrangement 35 may include a serated portion 63, as shown in FIGS. 2 and 4 that reduces or prevents compression of the porous arrangement.

Slide Support

An apparatus according to the invention also includes one or more slide supports. A group of the slides is then positioned by hand or mechanically on a slide support for further processing in the automated apparatus according to the invention. In preferred embodiments of the invention, a slide container includes guides suitable for positioning and/or retaining one or more slides. The slide support is preferably movable, i.e., adapted to rotate around an axis or be translated along a path. In accordance with the invention, the slide support is movable to determined positions or stages, including one or more stages that align a portion or portions of the support adjacent to or in proximity to another element of the automated apparatus, e.g., a loader or unloader.

In preferred embodiments of the invention, the slide support includes a plurality of radial projections adapted to receive a microscope slide with or without a filter. The slide support being rotatable about the same axis as the container support.

In accordance with preferred embodiments of the invention, the slide support is positionable at an intermediate level between the container support and the head assembly. In accordance with the invention, the microscope slide support is movable to determined positions, including one or more positions that align a portion or portions of the support adjacent to or in proximity to respective filters.

Fluid Movement Structures

In accordance with embodiments of the invention, the automated apparatus includes one or more elements for altering differential pressure within the apparatus so that the sample can move through a portion of the automated apparatus. In accordance with embodiments of the invention, the fluid component of the sample may be either gaseous or liquid, depending on the use. For example, inducing a vacuum in a conduit communicating with the sample container will draw the sample in the container through the filter assembly. It may also be desirable to induce a positive pressure to return any uncollected portions of the sample to the specimen container, or to move the filtered liquid to a disposal container or chamber. A reversible pump is one example of a preferred vacuum/pressure element.

Additionally, it may be desirable to clean or rinse a portion of a sub-assembly, e.g., a portion of the head assembly. In preferred embodiments of the invention, the pump or the like may move a rinse solution from a source container through a conduit to the head assembly. Included within the present invention are a variety of source containers, pressure differential generators, and conduits for establishing fluid communication between or to pre-selected elements of the automated apparatus.

Movement of a fluid through the system may be effected by maintaining a pressure differential between a source of fluid and a destination of the fluid. Exemplary means of establishing this pressure differential may be by applying pressure to any part of the system on the inlet side of the filter chamber; applying a vacuum to any part of the system on the outlet side of the filter chamber; or any form of pump, such as an autovial spunglass filter (manufactured by Genex Corporation); gravity head; or a flexible, collapsible container, such as a specimen container, which may be squeezed to force the sample through the filter.

Loaders

In accordance with preferred embodiments of the invention, at least one loader may be adjacent to or a part of the automated apparatus. It is intended that a variety of loaders may be used in conjunction with the operation of the automated apparatus. For example, an automated apparatus may include one or more of the following: a filter loader; a microscope slide loader; a specimen container loader; a capper, designed to position and place a cover on an open specimen container; a loader for positioning and matingly engaging a portion of the head assembly on a group of the specimen containers; a loader for positioning and matingly engaging a portion of each filter assembly to respective slides. Exemplary loaders are described in more detail below.

Unloaders

In accordance with preferred embodiments of the invention, at least one unloader may be adjacent to or a part the automated apparatus. It is intended that a variety of unloaders may be used in conjunction with the operation of the automated apparatus. For example, an unloader may be used for any element for which there is a loader, as described above. Exemplary unloaders are described in more detail below.

Tracking Mechanism

In accordance with preferred embodiments of the invention, the automated apparatus may include one or more tracking mechanisms for tracking the progress of a sample through the automated apparatus, and/or to track a sample after it has been processed by the automated apparatus. An exemplary tracking mechanism involves the use of a bar code. In this embodiment of the invention, the automated apparatus may include a bar code reader and a bar code printer. An exemplary tracking mechanism is described in more detail below.

Controllers

In accordance with preferred embodiments of the invention, the automated apparatus may include one or more controllers for selectively moving and positioning an element of the automated apparatus, for initiating or discontinuing an operation of the automated apparatus, or for monitoring the progress of the operation of the automated apparatus. An example of a preferred controller is a computer and computer program. Other uses of a controller will be evident to one skilled in the art, and are included within the invention. Exemplary controllers are described in more detail below.

Miscellaneous Structures

An automated apparatus according to the invention may also include a variety of movement transmissions including belts, motors, pulleys, anti-friction elements, lifters, transports, and supports, as well as conduits, a rinsing or cleaning head and its source or supply (e.g., container) of a rinsing or cleaning solution, a fixative applicator and its source or supply (e.g., container) of fixative solution, and the like to effect operation of the elements of the automated apparatus. Other additional or substituted structures will be evident to one skilled in the art, and are included within the invention. Exemplary structures are described in more detail below.

Stirring Mechanism

A mixer according to preferred embodiments of the invention may include an agitator for stirring each sample in its respective specimen container. As noted above, each head may include a portion that engages a stirring element extending into the sample. This portion of each head is adapted to be connected to a movement transmission, e.g. a motor rotating a belt, or the like that will rotate the portion of each head. The movement transmission may engage a single head, or preferably, engage all of the heads. The belt of a movement transmission may alternatively be activated by rotation of the specimen container supports around an axis.

Method of Operation

It will be clear from the description of the various elements of the automated apparatus that a wide variety of methods of operation may be used. An exemplary mode of operation is described below, and it is intended that the nature, sequence, and number of steps are exemplary.

A group of specimen containers containing respective samples are arranged on a container support, either manually or by a loader. In some embodiments of the invention, a technician enters into the controller one or more of the following parameters for each specimen container: specimen type (e.g., sputum, blood, urine, spinal fluid, etc.) mixing rate, mixing time, suction level, suction time, fixative (e.g., either a yes or no value), and drying time. After the appropriate parameters are loaded into the automated apparatus, the apparatus initiates sample processing. In preferred embodiments of the present invention, a bar code reader detects a bar code on each container, and the controller selects appropriate parameters based on bar coding on each container.

A filter assembly loader then positions the appropriate filter assembly (corresponding to information received from the bar code and the pre-selected parameters) into the respective filter chamber for each sample.

The container support is then advanced to a head stage, i.e. a predetermined position with respect to the head assembly, and the group of heads is then engaged with the corresponding group of containers.

Concurrently, a group of slides is arranged on the slide support in a pattern corresponding to the group of heads. The group of slides is advanced to a depositing stage wherein respective monolayers of particulate matter from each corresponding sample are transferred to the slide from its respective filter assembly.

The mixer is activated by the controller thus driving the agitators for stirring their respective samples. The controller then activates the pump to apply an appropriate vacuum in each head, thereby drawing at least a portion of each sample from its respective container.

After each sample has passed from the container through its respective filter assembly, the controller de-activates the pump, and the group of heads disengages from the corresponding group of containers.

The group of filters from their respective samples are transported to engage the corresponding group of slides, thereby transfering each monolayer of particulate matter to its respective slide, and then the filters are unloaded from their respective slides. In some embodiments of the invention, a portion of the filter assembly, typically the membrane portion, remains engaged with the microscope slide; in other embodiments, the entire filter assembly disengages from the microscope slide.

In preferred embodiments of the invention, a fixative applicator provides a supply of fixative to adhere the monolayer of particulate matter to its respective slide. The controller activates the fixative applicator, dispensing an appropriate amount (e.g., four drops) of fixative on the microscope slide.

In preferred embodiments of the invention, each microscope slide having a monolayer of particulate matter deposited thereon is marked, e.g. with a bar code, by a printer. Thus, each monolayer of particulate matter can be associated with its respective sample using the coding on the container and the slide.

In preferred embodiments of the invention, the slide support is advanced and the groups of slides are removed from the apparatus, either manually or with an unloader.

Preferred embodiments of the invention may also include a blower or drier for drying the surface of each microscope slide and/or removing, i.e. blowing off, any residual portion of the filter such as the membrane (if present). Again, the controller may coordinate the operation of the blower/drier with the operations of the other mechanisms and sub-assemblies of the apparatus.

Preferred embodiments may also include a rinsing cup which may then be aligned with each filter head. The controller activates the cleaning process so that any portion of each head requiring rinsing or cleaning is brought into contact with the cleaning solution.

Preferred embodiments may also include a sub-assembly for recovering each container with its original cover or with an unused cover. Used covers may be moved to a disposal area. The covered specimen containers may then be removed, either manually or with an unloader, from the automated apparatus for storage. Again, the controller would coordinate all automated operations associated with re-covering and storing the containers.

Exemplary Embodiments of the Invention

According to a first exemplary embodiment of the present invention shown in FIGS. 1–20, an automated apparatus 10 includes a group of specimen containers 20 arranged on a specimen container platform 100, a filter head assembly 40 positioned on a filter head support 200, and a microscope slide support 300. In the first exemplary embodiment of the invention, the specimen container support 100, the filter head support 200, and the microscope slide support 300 rotate around a central axis or shaft 11. As shown in FIGS. 1 and 2, the automated apparatus 10 may also include at least one filter assembly loader 50, microscope slide loader 70, microscope slide unloader 80, a bar code printer 90, a bar code reader 91, a fixative container 92, an air container 93, a rinsing liquid container 94, and cleaning liquid container 95, a waste container 96, and a controller 400.

Each of these elements will now be described in more detail.

Figure 3:
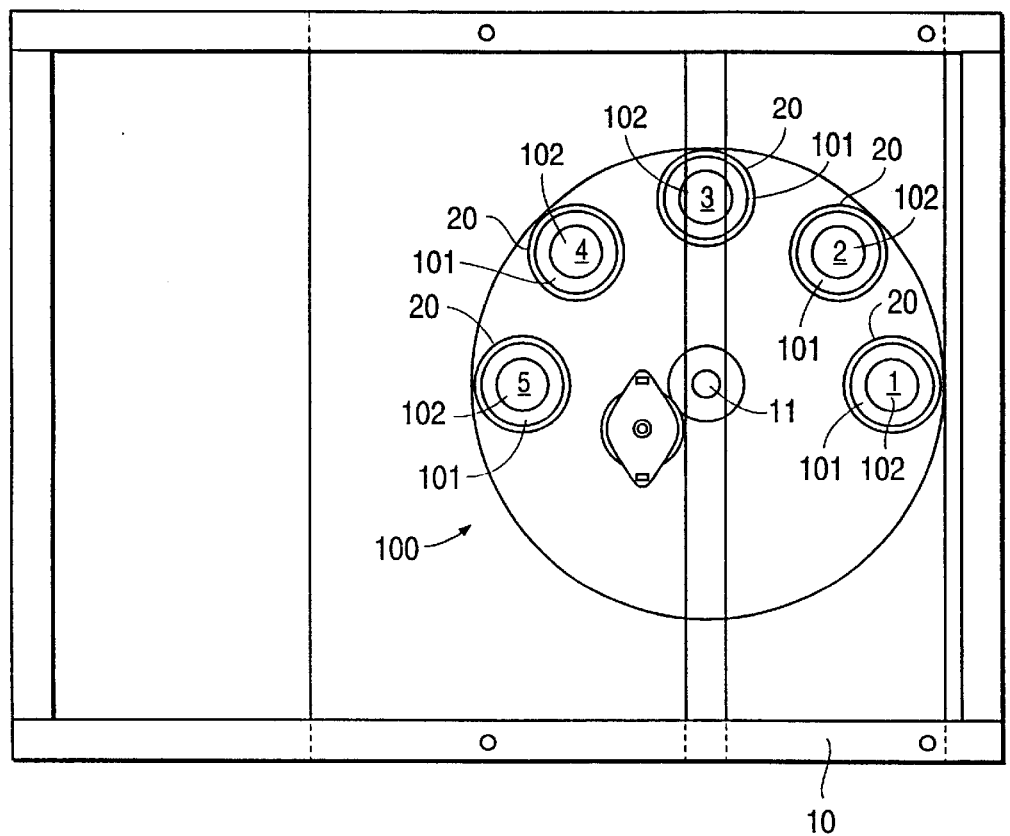
FIG. 3 is a top view of a specimen container holder assembly according to an embodiment of the invention.

The specimen container support 100 as illustrated includes a group of five recesses 101 adapted to receive and position a specimen container 20. As shown in FIG. 3, the recesses may be configured to receive more than one size specimen container, a large size 101 and smaller size 102. In the embodiment shown in FIGS. 3 and 4, the specimen container support 100 is circular and is movable up and down and axially around a central axis or shaft 11. To accommodate this movement, the automated apparatus may include one or more bearings 103 or the like, and a stepper 104 or similar element for moving the support 100 up and down the shaft 11. The specimen cup support 100 may move radially around the axis using a belt drive 105 or gear or the like.

The head assembly 200 as illustrated in FIG. 10 may include a lower portion 41 adapted to engage, position, and removably retain a filter assembly 33. In the first exemplary embodiment of the invention, the lower portion 41 is adapted to engage the filter assembly in a fluid tight or liquid tight seal, but such engagement is preferably releasable so that the filter assembly may be removed from the lower portion 41 during another step in the operation of the automated apparatus.

A portion of the head assembly 200 may include a gear or teeth 201 adapted to engage a belt or the like so that the lower portion 41 is rotatable. As noted above, this belt driven rotational movement is transferred to a portion of the specimen cup cover so that agitators extending into the container stir the sample.

The head assembly 200 also preferably includes a fitting 202 adapted to engage one or more conduits that establish fluid communication with at least one of an air container 93, a rinsing liquid container 94, a cleaning liquid container 95, and a waste container 96. The communication with the air container 93 may be used to disengage the filter assembly 33 from the portion 41 during another step in the operation of the automated device 10, or may be used to push a plunger or the like that pushes the filter assembly out of the portion 41.

As shown in FIG. 10, the filter head assembly may also include one or more springs 203 for engaging a portion of the specimen container or cover 97, one or more springs 204 for allowing a portion 41 of the filter head assembly to move resiliently, and one or more bearings 205 that allow rotary movement of a portion of the head assembly. In most preferred embodiments of the invention, the head assembly 200 comprises a cylinder within a cylinder construction.

Figure 5:
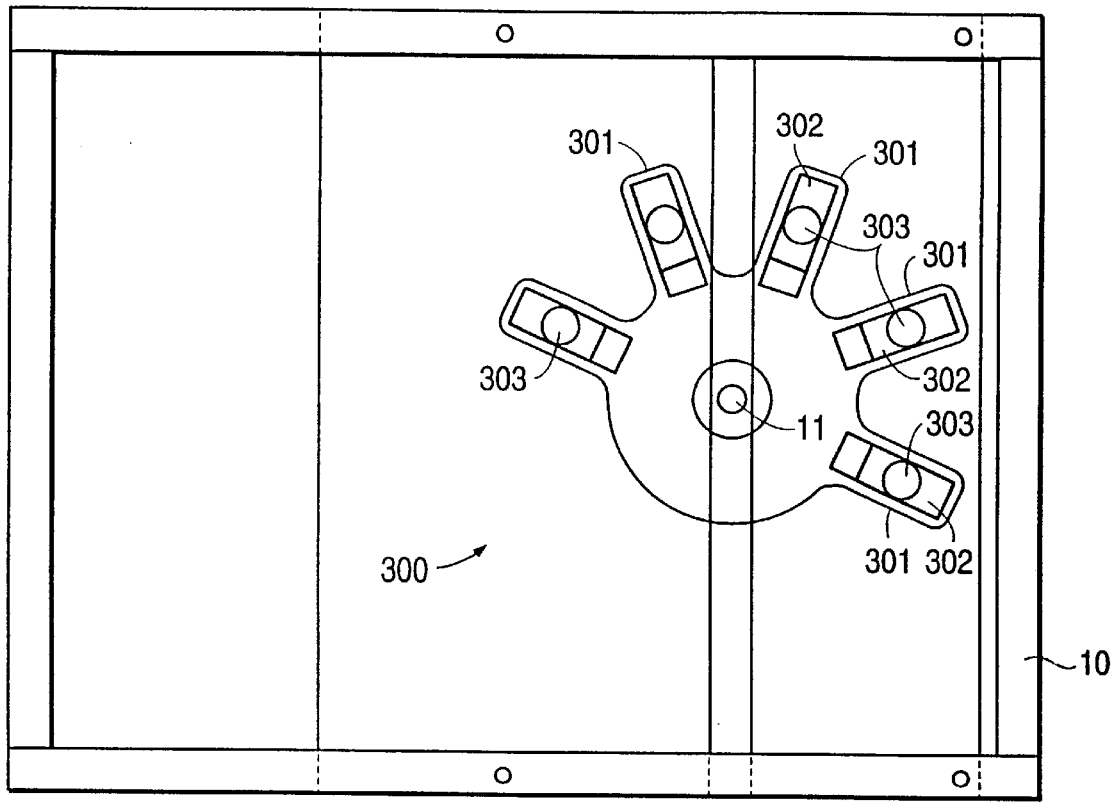
FIG. 5 is a top view of a microscope slide turntable assembly according to an embodiment of the present invention.
Figure 6:
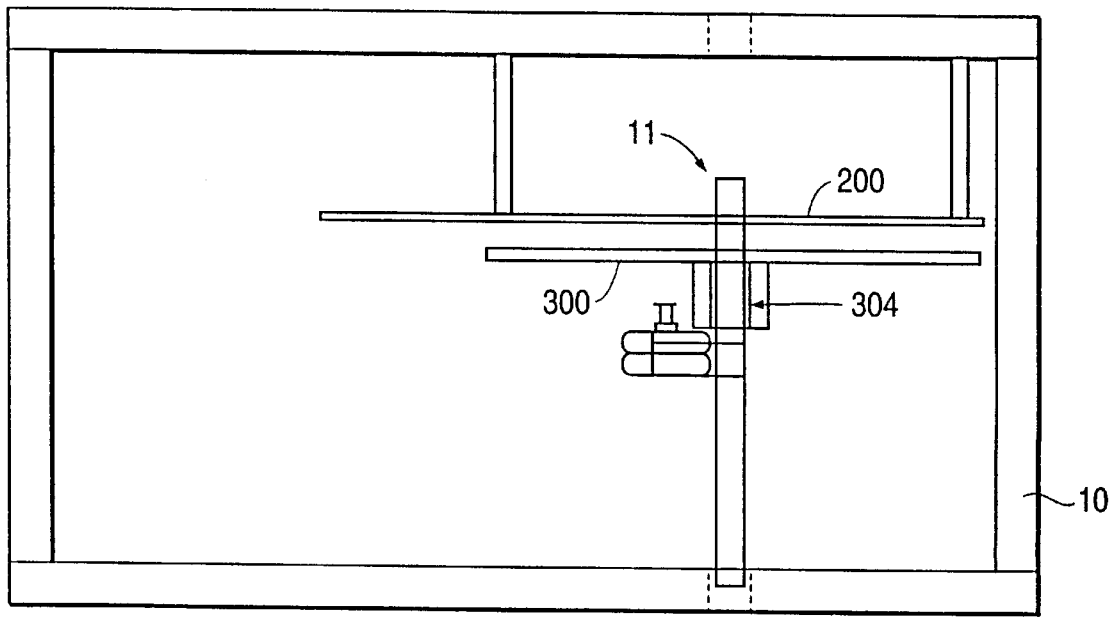
FIG. 6 is a side view of the assembly illustrated in FIG. 5.
Figure 7:
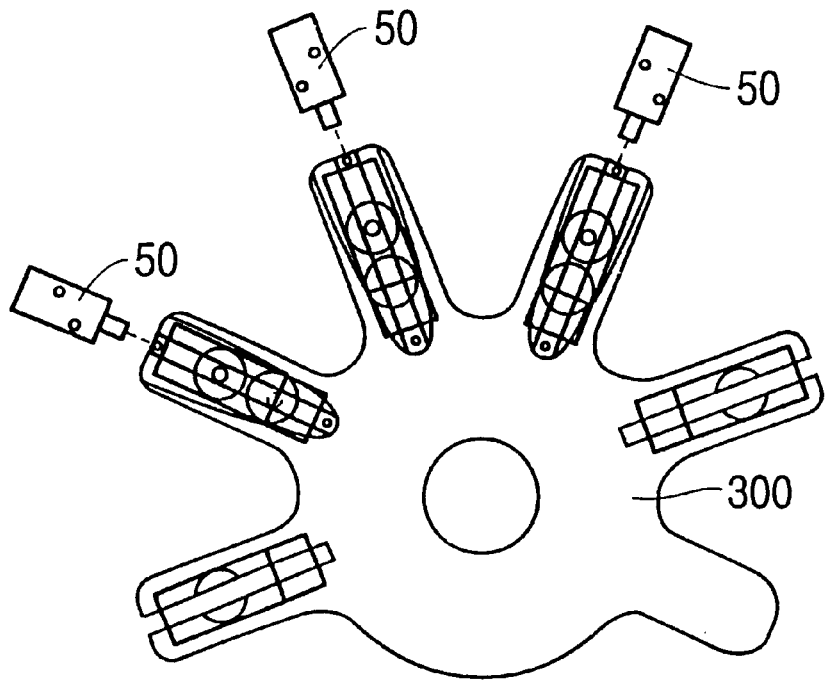
FIG. 7 is a top view of a filter loader assembly according to an embodiment of the present invention.

The microscope slide support 300, as shown in FIGS. 5–7 is adapted to receive a group of microscope slides and a group of filter assemblies 33. In a preferred embodiment of the invention, the support 300 includes radially extending projections 301. In a more preferred embodiment, each projection 301 includes a cavity or recess 302 adapted to receive and position a microscope slide, and each projection includes a cavity or recess 303 adapted to receive and position a filter assembly 33.

In accordance with the invention, the microscope slide support 300 is rotable around the axis 11 and vertically along the axis 11. Bearings may be provided that facilitate movement of the support 300, and may also support cantilever loads or pressure on the projections 301 of support 300. The support 300 may also be rotatable by a transmission such as a belt drive, gears, or the like; and movable vertically using a stepper or the like.

Figure 8:
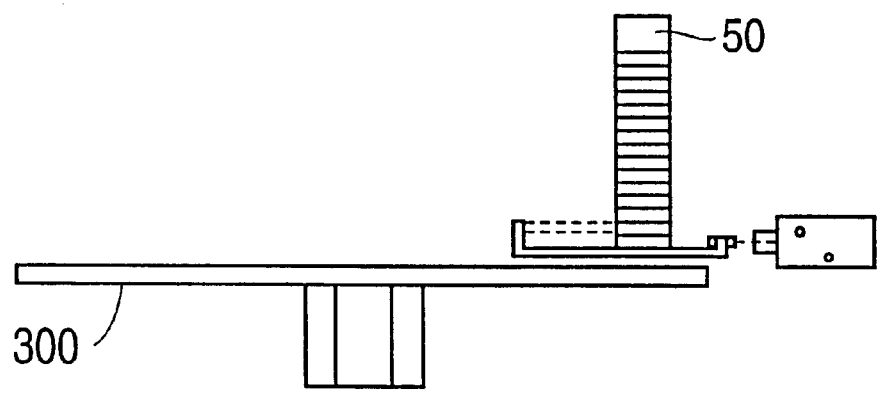
FIG. 8 is a side view of the assembly illustrated in FIG. 7.
Figure 9A:
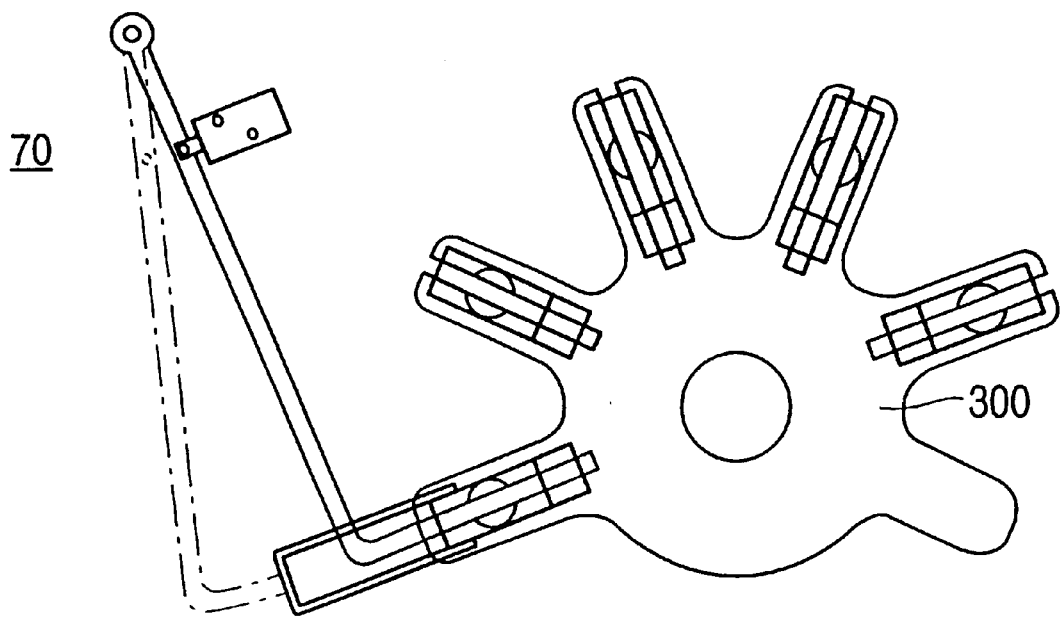
FIG. 9a is a top view of a microscope slide unloader assembly according to an embodiment of the invention.
Figure 9B:
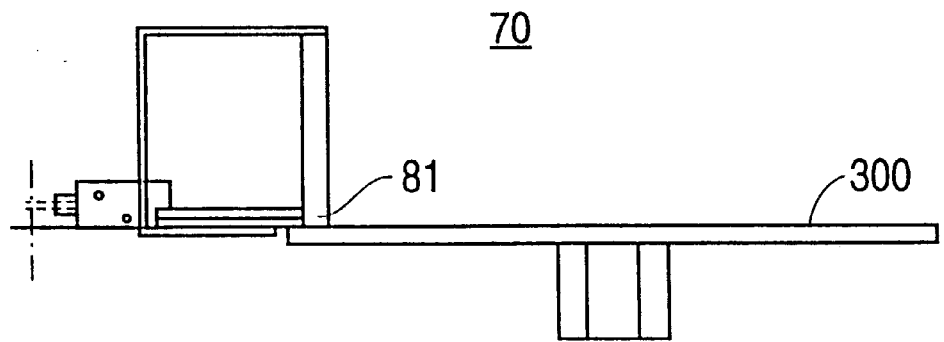

Filter loader assembly 50, as shown in FIGS. 2 and 8, preferably receives and positions groups of the filter assemblies 33, and is adapted to deposit one filter assembly 33 in a recess on the microscope slide support. In the first exemplary embodiment, filter assemblies 33 are stacked in a tube or channel, and a motor or solenoid moves a plate having a hole from a first position where the filter stack is closed to a second position where the filter stack is open. In the open position, a spring or the like may push a single filter assembly through the hole and onto the microscope slide support. Alternatively, the spring may be used to retain all but one of the filter assemblies, so that when the hole is aligned with the stack of filter assemblies, the unretained filter assembly is allowed to drop onto the microscope slide support.

The microscope slide loader 70 preferably retains and positions groups of microscope slides, and is adapted to move a single microscope slide onto a recess in the microscope slide support. In preferred embodiments, the slides are arranged in a tube having a closed bottom end, and, adjacent to the bottom end, one or more slots 81 through which a single microscope slide can pass. An arm on the slide loader pushes a slide from the stack and onto the microscope slide support. When the arm retracts, the next microscope slide drops into position.

The present invention also includes a method for removing particulate matter from a sample, and for transferring a monolayer of the particulate matter, such as cells, to a microscope slide. According to preferred embodiments of the present invention, membrane filtration provides a method of depositing cells evenly over a microscope slide with minimal overlap. This allows for clear observation and optimal diagnostic accuracy.

An exemplary method of using the invention includes collecting a sample containing particulate matter in a collection container 20. The container 20 is then capped with a cover assembly 500 that includes one or more of the following: base 31, well 501, and at least a portion of the filter chamber 30.

Figure 13:
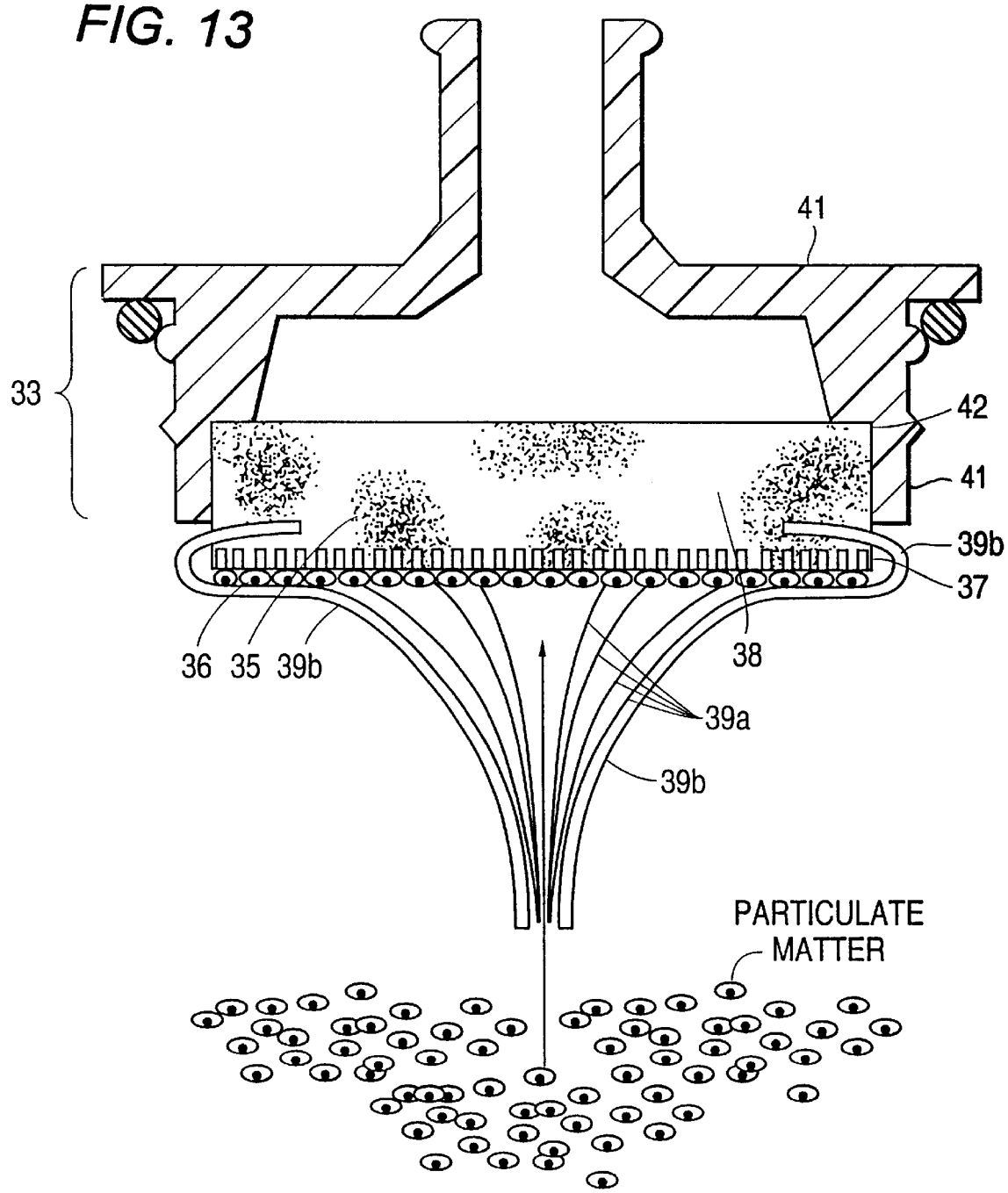
FIG. 13 is an exploded side view of the filter assembly according to an embodiment of the invention.

When the sample is pulled from the container 20, fluid will flow through porous arrangement 35 as shown in FIGS. 13 and 14, so that a monolayer of particulate matter is formed on collection site 36. Once the monolayer of cells is formed, fluid flow is reduced in the center of porous arrangement 35 and increases towards the edges of the porous arrangement. At least in part this is due to the blockage of flow by the collected cells as they form the monolayer on the surface of the porous arrangement. When the monolayer has mostly covered the surface 45 of the porous arrangement, the flow bypasses the first porous medium and passes through the extended side area of the second porous medium. Thus, the area of the second porous medium extending beyond an end wall or skirt of the top portion acts as a vent (with low resistance to flow) which prevents cells piling up or collecting in more than a monolayer. Fluid may be passed back and forth through the porous arrangement as many times as desirable.

The first porous medium may then be pressed against a microscope slide to transfer the monolayer of particulate matter on the collection site onto the slide. This allows a cytological examination to be performed on the cells by a practitioner without the interference of the pores in the membrane or delay due to processing requirements.

A second exemplary embodiment of the present invention shown in FIGS. 21–26C. A container support 100' arranges a group of three containers 20 in a linear pattern. The container support 100' cooperatively retains the containers 20 so as to prevent relative rotation between the containers 20 and the container support 100'.

Figure 22:
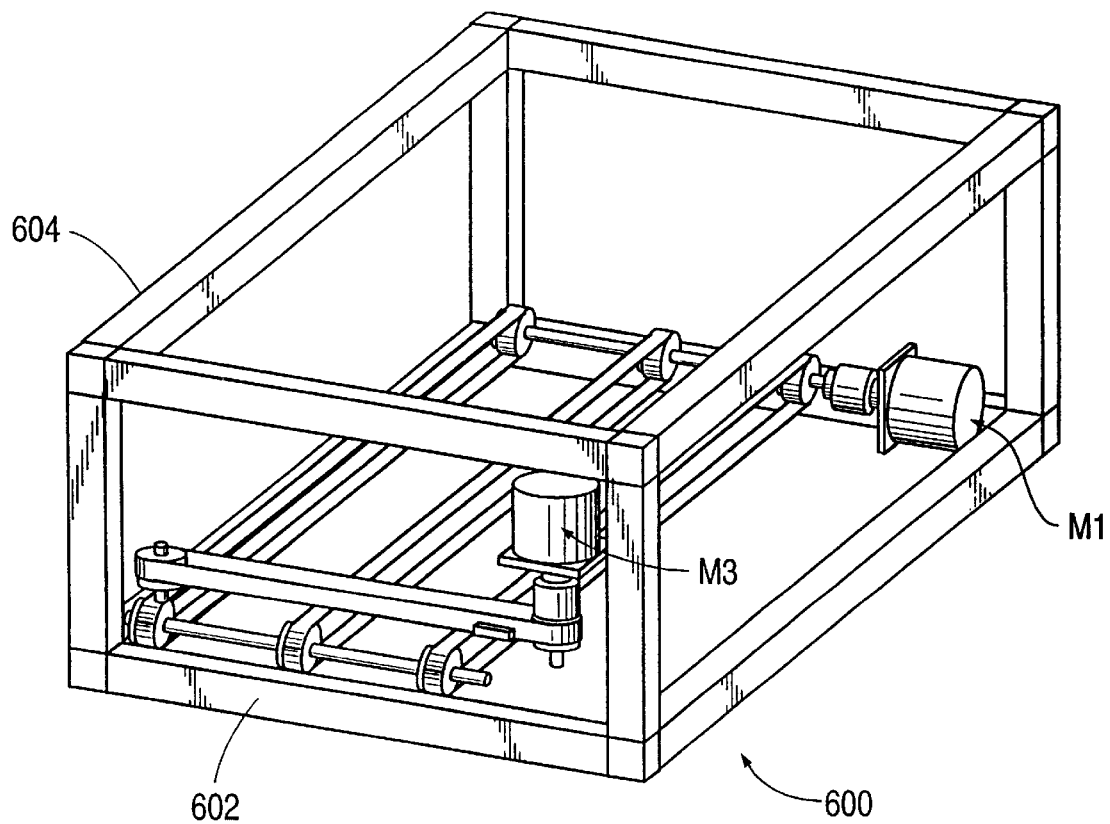
FIG. 22 is a perspective view of a first conveyer according to an embodiment of the invention.

FIG. 22 shows a container conveyor system 600 for advancing groups of containers 20 in their respective container supports 100'. A first transmission, including a motor M1 driving at least one belt (three are shown), advances container supports 100' toward a front 602 of the conveyor system 600. A second transmission, including a motor M3 driving at least one belt, sequentially advances individual ones of the container supports 100' out a side 604 of the conveyor system 600 to the head stage of the invention.

Figure 23:
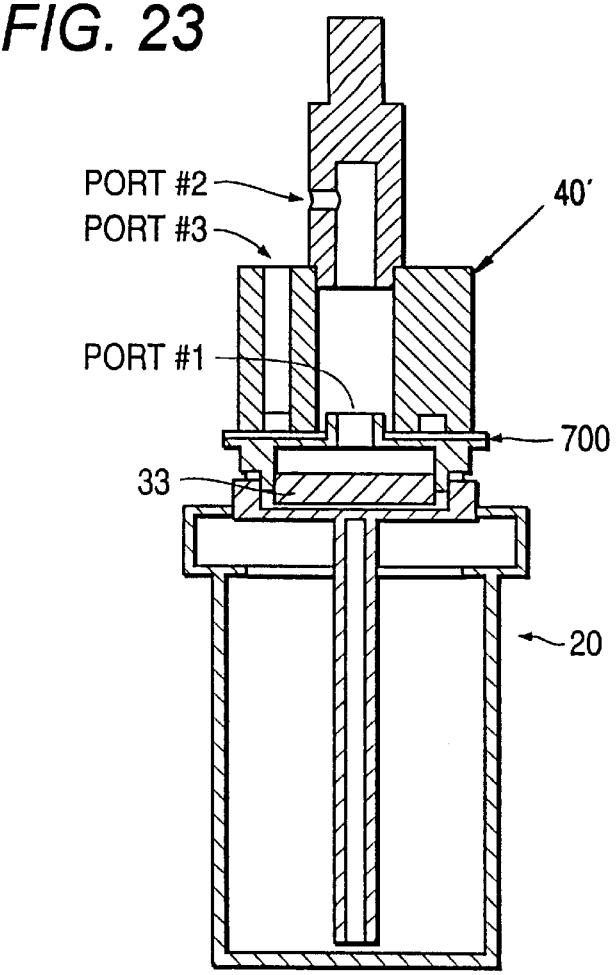
FIG. 23 is a crossection view of a detail of an embodiment of the invention at the head stage.

As shown in FIG. 23, an adapter 700 matingly engages the container 20. The adapter 700 fixedly retains filter assembly 33, and is frictionally retained with respect to the container 20. The head 40' includes three ports: a first port for communicating with the sample via the adapter 700, a second port for communicating with the pump, and a third port for releasably engaging the adapter 700 to the head 40'. Connecting a vacuum source to the third port will cause the adapter 700 to adhere to the head 40', enabling head 40' to separate adapter 700 from container 20 against the frictional opposition retaining the adapter 700 with respect to the container 20. Disconnecting the vacuum source will allow gravity to separate the adapter 700 from the head 40', thus allowing the filter 33 to be positioned on its respective slide.

Figure 24:
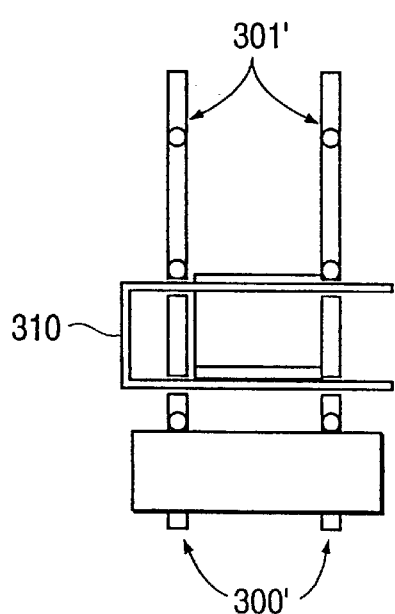
FIG. 24 is a top view of a slide loader according to an embodiment of the invention.
Figure 25:
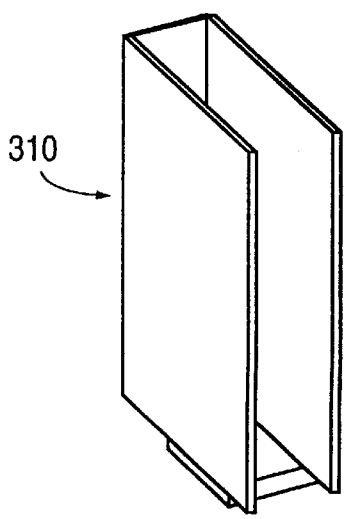
FIG. 25 is a perspective view of a detail of the loader illustrated in FIG. 24.

FIGS. 24 and 25 show a slide support, conveyor, and loader system wherein at least one slide support belt 300' (two are shown) support a group of slides arranged in a determined pattern. Projections 301' on the slide supports 300' sequentially remove slides from a slide supply 310. The spacing and linear arrangement of the slides on the slide support belts 300' correspond to the spacing and linear arrangement of the group of containers 20 in each container support 100'.

Figure 26A:
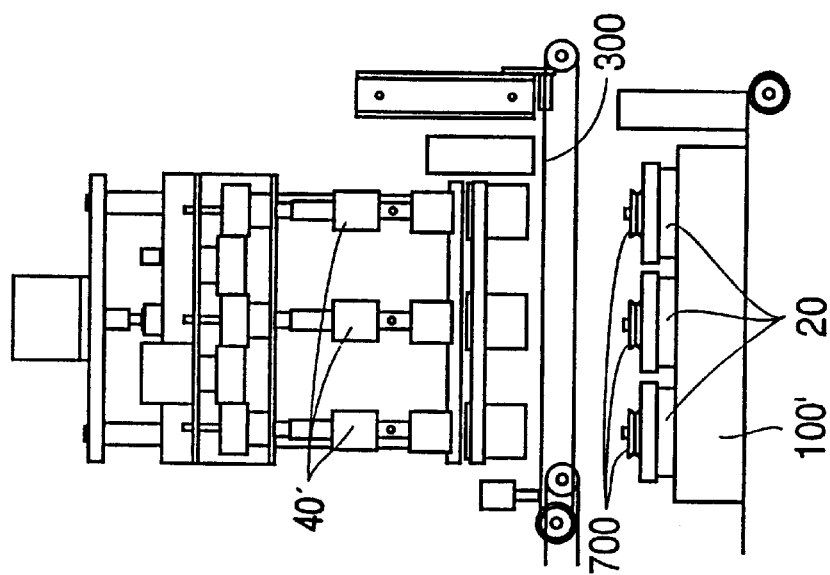
FIG. 26A is a schematic illustration according to an embodiment of the invention showing a group of containers advanced to the head stage.
Figure 26B:
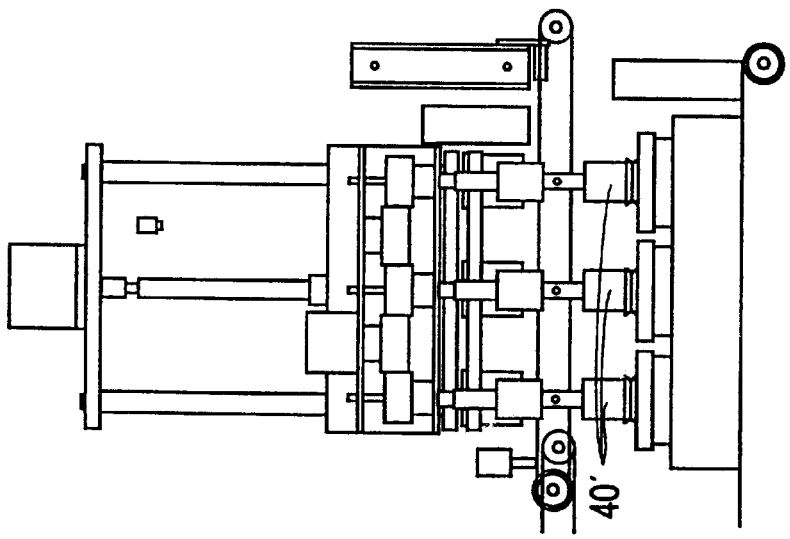
FIG. 26B is a schematic illustration according to an embodiment of the invention showing a group of heads in fluid communication with corresponding containers at the head stage.
Figure 26C:
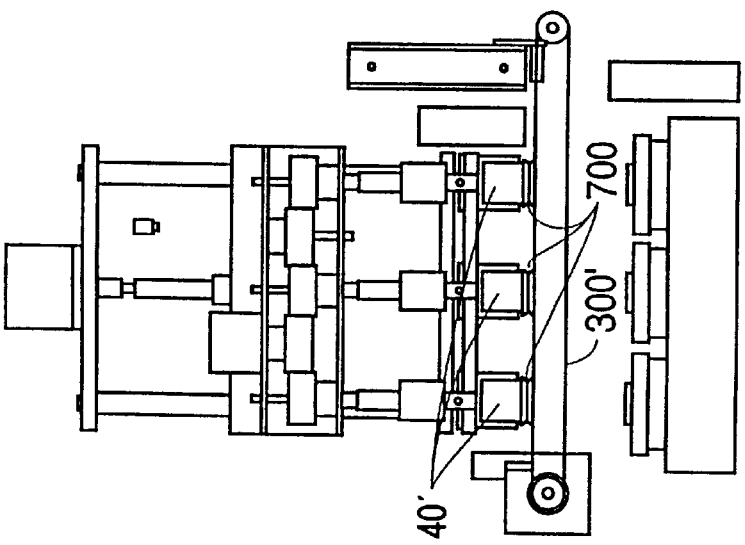
FIG. 26C is a schematic illustration according to an embodiment of the invention showing monolayers of particulate matter from respective samples being transferred to a group of slides corresponding to respective heads.

A method of using the second exemplary embodiment is illustrate in FIGS. 26A–26C. In FIG. 26A, a group of containers 20 in a container support 100' have been advanced by the second transmission to the head stage. The group of heads 40' corresponding to the group of containers 20 are aligned and spaced apart from their respective adapters 700. The slide support belts 300' extend parallel to the groups of containers and slides and are laterally located on opposite sides of the group of adapters 700.

In FIG. 26B, the group of heads 40' have been displaced so as to engage their respective adapters 700. A vacuum source is connected to the third port to securely connect each head 40' to its respective adapter 700. The sample is mixed by rotating each head 40' relative to its respective container, thereby causing the agitator in each sample to disperse the particulate matter. A vacuum source is connected to the second ports of each head 40' to draw at least a portion of the sample in each container 20 through its respective filter 33 thereby collecting a monolayer of particulate matter.

In FIG. 26C, the heads 40' are displaced apart from their respective containers 20. Each adapter 700 is securely retained relative to their respective head 40' by virtue of the vacuum source connected to the third ports of each head 40'. The slide support belts 300' are activated to arrange a slide with respect Alternative Configurations The cytology collection apparatus 10 preferably includes an easily openable filter chamber. Preferably, the chamber comprises a simple two-piece construction including a first detachable portion 44 and a second detachable portion 42, as shown in FIG. 2. The first chamber portion 42 having a first port 41. The first chamber portion 42 includes a recess 50.

Porous arrangement 35 may include a unitary structure having a first portion of density and/or pore size suitable to prevent the passage of cells therethrough and a second portion of density and/or pore size suitable for passing the fluid therethrough.

In preferred embodiments, the porous arrangement includes a first porous medium comprising a porous polycarbonate membrane, suitable for preventing the passage of cells therethrough. The porous arrangement may further include second porous medium comprising a depth filter, or frit. The frit may be made of polypropylene or high density polyethylene POREX7 porous plastics.

It should be noted that various types of porous arrangements can be used interchangeably with that of the present embodiment. While a polycarbonate membrane is especially suitable for use in the cytology collection apparatus of the present invention, other porous membranes are also suitable. Exemplary porous membranes are well known in the art, and are disclosed in U.S. Pat. Nos. 5,471,994 and 5,301,685, both hereby incorporated by reference.

The porous membrane preferably has a pore size from about 0.22 microns to about 8 microns, more preferably from about 1 micron to about 6 microns, most preferably about 2 microns, which allows it to trap cells which are more than 3 microns in size. The membrane is suitable to allow fluid flow to pass therethrough while preventing the passage of particulate matter. The second porous medium is suitable for passing fluid therethrough and may also be capable of removing particulate matter from the sample. The pore size of the second porous medium may range from about 5 microns to about 60 microns, preferably from about 15 microns to about 45 microns, most preferably about 35 microns.

As one skilled in the art will recognize, adjusting the pore size of the porous membrane and the porous depth filter in accordance with the type and/or size of matter to be collected permits the collection of the matter on the collection site 14. In preferred embodiments of the invention, the pore size is chosen so that a uniform layer of matter, preferably a monolayer of matter, is formed on the collection site. For example, from about 3 $\mu$m to about 40 $\mu$m or more has been shown to be effective, but it is intended that the invention should not be limited to a certain range of pore size.

In most preferred embodiments of the invention, first porous medium 37 is attached to second porous medium 38 using an adhesive that is soluble in the sample. Such soluble adhesives include but are not limited to sugar compositions, gels, and the like.

Preferrably, the first port 54 is be configured as a connector adapted to be connected to a container. Second port 41 may be configured as a connector and may be adapted for connect to a vacuum/pressure source, e.g. a reversible pump.

While the cytology collection apparatus 10 can be used for any biological fluid, it is particularly useful for preparing test samples from urine and its associated cells, and for Pap smears.

The matter collection apparatus or module described above may be used in combination with other suitable filtration or treatment devices. Exemplary devices include other debris and/or assay devices or modules which may be attached to housing 10. Typically, these additional modules will include a housing having an inlet and an outlet, and will include a filtration, assay, or detection element positioned across the fluid flow path in the housing. For example, the apparatus may comprise a housing including inlet and outlet ports defining a flow path between the inlet and the outlet; a filter positioned across the flow path; and a freely movable chromatography/assay element, such as substrate beads, positioned on the outlet side of the filter. The chromatography/assay element can freely mix with the matter in the fluid, capture the matter, and can then be assayed for the presence of the matter. Suitable devices include those disclosed in U.S. Pat. Nos. 4,953,561; 5,224,489; 5,016,644; 5,139,031; 5,301,685; 5,042,502; and 5,137,031, all incorporated herein by reference.

The cytology collection apparatus 10 of the present invention also permits isolation and collection of fresh cells and/or microorganisms from biological fluids to perform DNA probe and chromosomal analysis once the cells are hemolyzed by the proper buffer.

The most widely used stain for visualization of cellular changes in cytology is the Papanicolaou staining procedure. This stain, which is used for both gynecologic and non-gynecologic applications, is basically composed of blue nuclear and orange, red and green cytoplasmic counterstains. The nuclear stain demonstrates the chromatic patterns associated with normal and abnormal cells, while the cytoplasmic stains help to indicate cell origin. The success of this procedure can be attributed to the ability to observe a number of factors, including definition of nuclear detail and cell differentiation. This staining procedure also results in a multicolor preparation that is aesthetic, possibly reducing eye strain.

Since cellular detail is dependent on fixation, it is preferred that cells be fixed immediately after being deposited on the slide. Too long a delay between preparation and fixation may expose the cells to drying, which may be detrimental to the cellular structure. Moreover, air drying artifacts can adversely affect the subsequent staining results. An exception is when the cells are stained with Wright-Giemsa Staiu, where air drying is used as the fixation step.

In an another embodiment of the present invention, the monolayer of cells may be fixed directly on the collection site. This may be carried out by first depositing a monolayer of cells on the collection site of the cytology collection apparatus as described above and subsequently passing a solution containing a fixative, such as alcohol or acetone, through the cytology collection apparatus.

Included within the scope of the present invention is the production of multiple specimens from a single patient sample. Additional slides for other stain applications can be easily prepared. Human papilloma virus testing, for example, by newer methods such as immunocytochemistry or in-situ hybridization can be performed on the additional slides. As oncogene products or other immunocytochemical tests are developed, more slides may be necessary. The different fixations that these tests may need can easily be incorporated into the procedure since the invention does not require the slides to be fixed in only one way.

This same slide preparation procedure can be used for virtually all forms of cytology. Furthermore, the use of completely contained disposable components addresses biohazard concerns. Ultimately, the enhanced presentation of cells, yielding improved cytologic interpretation, may expand the role of cytology by providing more consistent and reliable patient diagnosis.

Also, captured microorganisms can be cultured in culture medium. After a monolayer of cells has been collected in the cytology collection apparatus, fluid may be used to back-flush the collection site, thereby transferring any collected microorganisms from the collection site.

In bacteria testing, the first porous medium can be used for culturing with a Qualture device (not shown) to determine the presence of specific bacteria colonies. The Qualture device is a plastic capsule containing a filter membrane and four nutrient pads of dehydrated, selective media.

The Qualture technique is more sensitive than the agar plate method and more rapid in determining a presumptive diagnosis. The device screens, isolates and presumptively diagnoses bacterial isolates in one step, most often in 4–6 hours. Tests have demonstrated that recovery from fifty milliliters of fluid is excellent and sensitive.

Although the present invention has been described in terms of a particular preferred embodiments, it is not limited to those embodiments. Alternative embodiments, examples, and modifications which would still be encompassed by the invention may be made by those skilled in the art, particularly in light of the foregoing teachings.

Additional advantages and modifications will readily occur to those skilled in the art. Therefore, the invention in its broader aspects is not limited to the specific details, and representative devices, shown and described herein. Accordingly, various modifications may be made without departing from the spirit and scope of the general inventive concept as defined by the appended claims and their equivalents.

What is claimed is:

1. An automated apparatus for batch processing a set of samples in respective containers, a monolayer of particulate matter from each sample being deposited on a corresponding slide for examination, the apparatus comprising:

a container support arranging a group of containers in a first pattern;

a first conveyer advancing said container support to a head stage;

a group of heads corresponding to said group of containers and engaging respective containers at said head stage, each of said group of heads communicating with its respective sample;

a pump producing a flow of each sample from its respective container through its respective head;

a group of filters corresponding to said group of heads, each of said filters communicating with said flow of its respective sample and including:

a membrane being interposed in a first branch of its respective sample flow and adapted for collecting its respective monolayer of particulate matter; and a frit being interposed in a second branch of its respective flow circumventing said membrane;

a slide support arranging a group of the slides in a second pattern, said group of the slides corresponding to said group of heads;

a second conveyer advancing said slide support to a deposit stage; and a controller coordinating each of said first conveyor advancing said container support, said group of heads engaging said group of the containers, said pump producing said flow of each sample, and said second conveyer advancing said slide support engagement;

wherein said controller is adapted for coordinating automatic sample throughput and correlating each sample container with a corresponding slide.

2. The automated apparatus according to claim 1, wherein said first pattern corresponds to said second pattern.

3. The automated apparatus according to claim 1, further comprising:

a mixer moving each of said heads relative to its respective container;

wherein said controller additionally coordinates said mixer moving each of said heads relative to its respective container with said group of heads engaging said group of the containers.

4. The automated apparatus according to claim 3, further comprising:

a drive rotating each of said heads;

wherein each of said group of the containers is fixed with respect to said container support.

5. The automated apparatus according to claim 3, further comprising:

a drive rotating each of said group of the containers relative to said container support;

wherein each of said heads is prevented from rotating.

6. The automated apparatus according to claim 3, further comprising:

a group of agitators corresponding to said group of heads, each of said agitators communicating with its respective sample in its respective container and adapted for stirring its respective sample so as to disperse its respective particulate matter.

7. The automated apparatus according to claim 1, further comprising:

a container loader placing said group of the containers on said container support in said first pattern;

wherein said controller additionally coordinates said container loader arranging said group of the containers on said container support with said first conveyer advancing said container support.

8. The apparatus according to claim 1, further comprising:

a container unloader removing said group of the containers from said container support at a container unloading stage;

wherein said first conveyer advances said container support from said head stage to said container unloading stage; and wherein said controller additionally coordinates said container unloader removing said group of the containers from said container support with said first conveyer advancing said container support.

9. The automated apparatus according to claim 1, further comprising:

a slide loader arranging said group of the slides on said slide support in said second pattern;

wherein said controller additionally coordinates said slide loader arranging said group of the slides on said slide support with said second conveyer advancing said slide support.

10. The automated apparatus according to claim 1, further comprising:

a slide unloader removing the slides from said slide support at a slide unloading stage;

wherein said second conveyer advances said slide support from said deposit stage to said slide unloading stage; and wherein said controller additionally coordinates said slide unloader removing said group of the slides from said slide support with said second conveyer advancing said slide support.

11. The automated apparatus according to claim 1, further comprising:

a reader detecting first identifiers on the respective containers; and a printer marking second identifiers on the respective slides;

wherein said first and second identifiers associate the sample in the respective container with the monolayer of particulate matter on the respective slide; and wherein said controller additionally coordinates said reader detecting said first identifiers on the respective containers with said printer marking said second identifiers on the respective slides.

12. The automated apparatus according to claim 1, wherein said group of heads reciprocate with respect to said group of the containers along a path, and wherein said deposit stage lies along said path.

13. The automated apparatus according to claim 1, further comprising:

a plurality of filter sources each supplying a different one of said filters; and a filter loader transporting each said filter from one of said plurality of filter sources to a filter chamber formed by each of said group of heads engaging its respective container;

wherein said controller additionally coordinates said filter loader transporting said filters from said plurality of filter sources with said group of heads engaging said group of containers.

14. The automated apparatus according to claim 1, further comprising:

an applicator supplying a fixative adapted for securing the monolayer of particulate matter on the slide;

wherein said controller additionally coordinates said applicator supplying a fixative with said second conveyer advancing said slide support.

15. The automated apparatus according to claim 14, further comprising:

a blotter absorbing excess fixative;

wherein said controller additionally coordinates said blotter absorbing excess fixative with said applicator supplying a fixative.

16. The automated apparatus according to claim 14, further comprising:

a blower drying said fixative;

wherein said controller additionally coordinates said blower drying said fixative with said applicator supplying a fixative.

17. The automated apparatus according to claim 1, further comprising:

a blower separating said membrane from the monolayer of particulate matter on the slide;

wherein said controller additionally coordinates said blower separating said membrane from the monolayer of particulate matter on the slide with said second conveyer advancing said slide support.

18. The apparatus according to claim 1, further comprising:

a solution bath for cleaning said group of heads;

wherein said controller additionally coordinates said solution bath for cleaning said group of heads with said group of heads engaging said group of containers.

19. The apparatus according to claim 1, wherein said pump returns an uncollected portion of each sample to its respective container.

20. The apparatus according to claim 1, wherein said first and second branches of each said flow pass through said frit for its respective sample.

21. An automated method for batch processing a set of samples in respective containers, a monolayer of particulate matter from each sample being deposited on a corresponding slide for examination, the method comprising:

attaching a group of heads to a corresponding group of sample containers, each of said group of heads communicating with its respective sample;

pumping a flow of each sample from its respective container through its respective head;

filtering each said flow with a respective one of a group of filters corresponding to said group of heads, said filtering including:

collecting the monolayer of particulate matter with a membrane in a first branch of each said flow; and circumventing said membrane through a frit in a second branch of each said flow;

transferring each said membrane with its respective monolayer of particulate matter to a respective one of a group of slides, said group of slides corresponding to said group of heads; and controlling coordination of each of said attaching, pumping, filtering, and transferring operations to automatically deposit the monolayer of particulate matter from its respective sample to its respective slide.

22. The automated method according to claim 21, further comprising:

concurrently processing new groups of the containers in different ones of said attaching, pumping, filtering, and transferring operations; and repeating said operations of attaching, pumping, filtering, and transferring for each new group of the containers;

wherein said controlling additionally coordinates said concurrent processing of each group of the containers with said operations of attaching, pumping, filtering and transferring.

23. The automated method according to claim 21, further comprising:

arranging said group of containers on a container support in a pattern; and advancing said container support with a conveyer to said engaging operation;

wherein said controlling additionally coordinates said arranging said group of containers and advancing of said container support with said attaching, pumping, filtering and transferring operations.

24. The automated method according to claim 21, further comprising:

removing said group of containers from said container support;

wherein said controlling additionally coordinates said removing of said group of containers with said attaching, pumping, filtering and transferring operations.

25. The automated method according to claim 21, further comprising:

arranging said group of slides on a slide support in a pattern; and advancing said slide support with a conveyer to said transferring operation;

wherein said controlling additionally coordinates said arranging of said group of slides and advancing of said slide support with said attaching, pumping, filtering, and transferring operations.

26. The automated method according to claim 21, further comprising:

removing said group of slides from said slide support;

wherein said controlling additionally coordinates said removing of said group of slides with said attaching, pumping, filtering and transferring operations.

27. The automated method according to claim 21, further comprising:

mixing each sample in its respective container by moving each of said heads relative to its respective container;

wherein said controlling additionally coordinates said mixing with said attaching, pumping, filtering and transferring operations.

28. The automated method according to claim 26, wherein said mixing includes rotating each of said heads relative to its respective container.

29. The automated method according to claim 21, further comprising:

reading first identifiers on the respective containers; and printing second identifiers on the respective slides;

wherein said first and second identifiers associate the sample in the respective container with the monolayer of particulate matter on the respective slide; and wherein said controlling additionally coordinates said reading and printing with said attaching, pumping, filtering and transferring operations.

30. The automated method according to claim 21, further comprising:

selecting said filter from a plurality of filter sources; and transporting said filter from one of said plurality of filter sources to a filter chamber formed by each of said group of heads engaging its respective container;

wherein said controlling additionally coordinates said selecting and transporting with said attaching, pumping, filtering and transferring operations.

31. The automated method according to claim 21, further comprising:

applying a fixative to the monolayer of particulate matter on its respective slide;

wherein said controlling additionally coordinates said applying with said attaching, pumping, filtering and transferring operations.

32. The automated method according to claim 31, further comprising:

blotting excess fixative;

wherein said controlling additionally coordinates said blotting with said attaching, pumping, filtering, transferring and applying operations.

33. The automated method according to claim 31, further comprising:

drying said fixative with a blower;

wherein said controlling additionally coordinates said drying with said attaching, pumping, filtering, transferring and applying operations.

34. The automated method according to claim 31, further:

separating with a blower said membrane from its respective monolayer of particulate matter on the slide;

wherein said controlling additionally coordinates said separating with said attaching, pumping, filtering, transferring and applying operations.

35. The automated method according to claim 21, further comprising:

cleaning said group of heads in a solution bath;

wherein said controlling additionally coordinates said cleaning with said attaching, pumping, filtering and transferring operations.

36. The automated method according to claim 21, further comprising:

returning an uncollected portion of each sample to its respective container;

wherein said controlling additionally coordinates said returning with said attaching, pumping, filtering and transferring operations.

37. The automated method according to claim 36, further comprising:

storing the containers having their respective uncollected portions of each sample;

wherein said controlling additionally coordinates said storing with said attaching, pumping, filtering, transferring and returning operations.

38. The automated method according to claim 21, further comprising:

stacking the slides deposited with their respective monolayer of particulate matter;

wherein said controlling additionally coordinates said stacking with said attaching, pumping, filtering and transferring operations.

* * * * *